US008945471B2

(12) United States Patent
Pantazis et al.

(10) Patent No.: US 8,945,471 B2
(45) Date of Patent: Feb. 3, 2015

(54) MULTIPURPOSE ANALYSIS USING SECOND HARMONIC GENERATING NANOPROBES

(75) Inventors: Periklis Pantazis, Pasadena, CA (US); Sotirios Masmanidis, Pasadena, CA (US); Scott E. Fraser, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 269 days.

(21) Appl. No.: 12/690,863

(22) Filed: Jan. 20, 2010

(65) Prior Publication Data

US 2010/0233820 A1 Sep. 16, 2010

Related U.S. Application Data

(60) Provisional application No. 61/205,488, filed on Jan. 21, 2009, provisional application No. 61/206,960, filed on Feb. 6, 2009.

(51) Int. Cl.
*G01N 21/00* (2006.01)
*G01N 21/64* (2006.01)
*C12Q 1/68* (2006.01)
(Continued)

(52) U.S. Cl.
CPC .......... *G01N 21/6458* (2013.01); *C12Q 1/6818* (2013.01); *G01N 21/6428* (2013.01); *B82Y 15/00* (2013.01); *B82Y 20/00* (2013.01); *G01N 2021/6441* (2013.01); *G02F 1/37* (2013.01); *G02F 2202/36* (2013.01)
USPC ......... 422/82.05; 436/164; 436/172; 359/328

(58) Field of Classification Search
None
See application file for complete search history.

(56) References Cited

U.S. PATENT DOCUMENTS 5,538,898 A 7/1996 Wickramasinghe et al.
5,952,180 A 9/1999 Ju
(Continued)

FOREIGN PATENT DOCUMENTS

WO WO 2004/106896 * 12/2004 ............. G01N 15/00
WO WO-2008/140584 A2 11/2008
(Continued)

OTHER PUBLICATIONS

Pantazis et al. "Second harmonic generating (SHG) nanoprobes for in vivo imaging". 2010. PNAS. vol. 107, No. 3, pp. 14535-14540.*
(Continued)

*Primary Examiner* — Robert Xu
(74) *Attorney, Agent, or Firm* — KPPB LLP

(57) ABSTRACT

Second harmonic nanoprobes for multipurpose imaging of samples and a method of using such probes to monitor nucleotide sequencing in a Multi-SHG Detection Imaging (MSDI) modality and to monitor external electric field using voltage sensitive second harmonic generating (SHG) nanoprobes are provided. The SHG nanoprobes are comprised of various kinds of nanocrystals that do not possess an inversion symmetry and therefore are capable of generating second harmonic signals that can then be detected by conventional two-photon microscopy for in vivo imaging of biological processes and structures such as cell signaling, neuroimaging, protein conformation probing, DNA conformation probing, gene transcription, virus infection and replication in cells, protein dynamics, tumor imaging and cancer therapy evaluation and diagnosis as well as quantification in optical imaging for a wide-range of biological and non-biological processes and devices.

17 Claims, 19 Drawing Sheets

(51) Int. Cl.
   B82Y 15/00   (2011.01)
   B82Y 20/00   (2011.01)
   G02F 1/37    (2006.01)

(56) References Cited

U.S. PATENT DOCUMENTS

| | | | |
|---|---|---|---|
| 6,624,915 | B1 | 9/2003 | Kirkpatrick et al. |
| 7,009,700 | B2 | 3/2006 | Dubois et al. |
| 7,679,079 | B1 | 3/2010 | Marks et al. |
| 7,813,016 | B2 | 10/2010 | Pu et al. |
| 7,993,891 | B2 | 8/2011 | Roitman et al. |
| 2004/0023415 | A1 | 2/2004 | Sokolov et al. |
| 2004/0146460 | A1 | 7/2004 | Salafsky |
| 2005/0025422 | A1 | 2/2005 | Magnusson et al. |
| 2005/0186565 | A1 | 8/2005 | Malak |
| 2006/0228725 | A1 | 10/2006 | Salafsky |
| 2006/0289115 | A1 | 12/2006 | Zhao et al. |
| 2012/0141981 | A1 | 6/2012 | Pantazis et al. |
| 2013/0129628 | A1 | 5/2013 | Pantazis |

FOREIGN PATENT DOCUMENTS

| | | | |
|---|---|---|---|
| WO | WO-2010/090844 | A2 | 8/2010 |
| WO | 2010090844 | A3 | 11/2010 |
| WO | 2013078410 | A1 | 5/2013 |

OTHER PUBLICATIONS

Lander et al., "Initial sequencing and analysis of the human genome", Nature, Feb. 15, 2001, vol. 409, pp. 860-921.
Lippincott-Schwartz et al., "Studying Protein Dynamics in Living Cells", Nature, Jun. 2001, vol. 2, pp. 444-456.
Margulies et al., "Genome sequencing in microfabricated high-density picolitre reactors", Nature, Sep. 15, 2005, vol. 437, pp. 376-380.
McCaig et al., "Controlling Cell Behavior Electrically: Current Views and Future Potential", Physiol. Rev, 2005, vol. 85, pp. 943-978.
Michalet et al., "Quantum Dots for Live Cells, in Vivo Imaging, and Diagnostics", Science, Jan. 28, 2005, vol. 307, pp. 538-544.
Michalet et al., "The Power and Prospects of Fluorescence Microscopies and Spectroscopies", Annu. Rev. Biophys. Biomol. Struct., 2003, vol. 32, pp. 161-182.
Michler et al., "Quantum correlation among photons from a single quantum dot at room temperature", Nature, Aug. 31, 2000, vol. 406, pp. 968-970.
Millar, "Fluorescence studies of DNA and RNA structure and dynamics", Current Opinion in Structural Biology, 1996, vol. 6, pp. 322-326.
Miyawaki, "Innovations in the Imaging of Brain Functions Using Fluorescent Proteins", Neuron, Oct. 20, 2005, vol. 48, pp. 189-199.
Miyawaki, "Visualization of the Spatial and Temporal Dynamics of Intracelllular Signaling", Development Cell, Mar. 2003, vol. 4, pp. 295-305.
Nie et al., "Probing Single Molecules and Single Nanoparticles by Surface-Enhanced Raman Scattering", Science, Feb. 21, 1997, vol. 275, pp. 1102-1106.
Nirmal et al., "Fluorescence intermittency in single cadmium selenide nanocrystals", Nature, Oct. 31, 1996, vol. 383, pp. 802-804.
Nuccitelli, "A Role for Endogenous Electric Fields in Wound Healing", Curr Top Dev Biol, 203, vol. 58, No. 1, pp. 1-24.
Pantazis et al., "Localized multiphoton photoactivation of paGFP in *Drosophila* wing imaginal discs", Journal of Biomedical Optics, Jul./Aug. 2007, vol. 12, No. 4, pp. 1-1-1-7.
Pelton et al., "Evidence for a diffusion-controlled mechanism for fluorescence blinking of colloidal quantum dots", PNAS, Sep. 4, 2007, vol. 104, No. 36, pp. 14249-14254.
Peter et al., "Imaging molecular interactions by multiphoton FLIM", Biology of the Cell, 2004, vol. 96, pp. 231-236.
Piehler, "New methodologies for measuring protein interactions in vivo and in vitro", Current Opinion in Structural Biology, 2005, vol. 15, pp. 4-14.

Selvin, "The renaissance of fluorescence resonance energy transfer", Nature Structural Biology, Sep. 2000, vol. 7, No. 9, pp. 730-734.
Shaner et al., "A guide to choosing fluorescent proteins", Nature Methods, Dec. 2005, vol. 2, No. 12, pp. 905-909.
Shendure et al., "Accurate Multiplex Polony Sequencing of an Evolved Bacterial Genome", Science, Sep. 9, 2005, vol. 309, pp. 1728-1732.
Shendure et al., "Advanced Sequencing Technologies: Methods and Goals", Nature Reviews Genetics, May 2004, vol. 5, pp. 335-344.
Shendure et al., "Overview of DNA Sequencing Strategies", Current Protocols in Molecular Biology, Jan. 2008, pp. 7.1.1-7.1.11.
So et al., "Self-illuminating quantum dot conjugates for in vivo imaging", nature Biotechnology, Mar. 2006, vol. 24, No. 3, pp. 339-343.
Suhling et al., "Time-resolved fluorescence microscopy", Photochem, Photobiol. Sci., 2005, vol. 4, pp. 13-22.
Sun, "Higher Harmonic Generation Microscopy", Adv. Biochem Engin/Biotechnol, 2005, vol. 95, pp. 17-56.
Trifonov et al., "Ultrafast Energy Transfer and Structural Dynamics in DNA", J. Phys. Chem, 2005, vol. 109, pp. 19490-19495.
Truong et al., "The use of FRET imaging microscopy to detect protein-protein interactions and protein conformational changes in vivo", Current Opinion in Structural Biology, 2001, vol. 11, pp. 573-578.
Tsien, "Fluorescent Probes of Cell Signaling", Ann. Rev. Neurosci, 1989, vol. 2, pp. 227-253.
Venter et al., "The Sequence of the Human Genome", Science, Feb. 16, 2001, vol. 291, pp. 1304-1351.
Wallrabe et al., "Imaging protein molecules using FRET and FLIM microscopy", Current Opinion in Biotechnology, 2006, vol. 16, pp. 19-27.
Wang et al., "Non-blinking semiconductor nanocrystals", Nature, Jun. 4, 2009, vol. 459, pp. 686-689.
Whitesides, "The 'right' size in nanobiotechnology", Nature Biotechnology, Oct. 2003, vol. 21, No. 10, pp. 1161-1165.
Zal et al., "Using live FRET imaging to reveal early protein-protein interactions during T cell activation", Current Opinion in Immunology, 2004, vol. 16, pp. 418-427.
Zhou et al., "Electrical signals control wound healing through phosphatidylinositol-3-OH kinase-γ and PTEN", Nature, Jul. 27, 2006, vol. 442, pp. 457-460.
Averitt et al., "Linear optical properties of gold nanoshells", J. Opt. Soc Am, Oct. 1999, vol. 16, No. 10, pp. 1824-1832.
Baker et al., "Imaging Brain Activity with Voltage-and Calcium-Sensitive Dyes", Cellular and Molecular Neurobiology, Apr. 2005, vol. 25, No. 2, pp. 245-282.
Bannai et al., "Imaging the lateral diffusion of membrane molecules with quantum dots", Nature Protocols, 2006, vol. 1, No. 6, pp. 2628-2634.
Bastiaens et al., "Fluorescence lifetime imaging microscopy: spatial resolution of biochemical processes in the cell", trends in Cell Biology, Feb. 1999, vol. 9, pp. 48-52.
Billinton et al., "Seeing the Wood through the Trees: A Review of Techniques for Distinguishing Green Fluorescent Protein from Endogenous Autofluorescence", Analytical Biochemistry, 2001, vol. 291, pp. 175-197.
Blanchard et al., "Eliminating membrane depolarization caused by the Alzheimer peptide (Aβ(1-42, aggr.)", Biochemical and Biophysical Research Communications, 2002, vol. 293, pp. 1204-1208.
Bosnjak et al., "Towards preventive medicine", EMBO reports, 2008, vol. 9, No. 11, pp. 1056-1060.
Braslavsky et al., "Sequence information can be obtained from single DNA molecules", PNAS, Apr. 1, 2003, vol. 100, No. 7, pp. 3960-3964.
Brauns et al., "Complex Local Dynamics in DNA on the Picosecond and Nanosecond Time Scales", Physical Review Letters, Apr. 15, 2002, vol. 88, No. 15, pp. 158101-1-158101-4.
Bruchez,Jr. et al., "Semiconductor Nanocrystals as Fluorescent Biological Labels", Science, Sep. 25, 1998, vol. 281, pp. 2013-2016.
Callender et al., "Fast Events in Protein Folding: The Time Evolution of Primary Processes", Annu. Rev. Phys. Chem, 1998, vol. 49, pp. 173-202.

(56) References Cited

OTHER PUBLICATIONS

Campagnola et al., "Second-harmonic imaging microscopy for visualizing biomolecular arrays in cells, tissues and organisms", Nature Biotechnology, Nov. 2003, vol. 21, No. 11, pp. 1356-1360.
Campagnola et al., "Second-harmonic imaging microscopy of living cells", Journal of Biomedical Optics, Jul. 2001, vol. 6, No. 3, pp. 277-286.
Chan et al., "Quantum Dot Bioconjugates for Ultrasensitive Nonisotopic Detection", Science, Sep. 25, 1998, vol. 281, pp. 2016-2018.
Cheatham, III, "Simulation and modeling of nucleic acid structure, dynamics and interactions", Current Opinion in Structural Biology, 2004, vol. 14, pp. 360-367.
Chen et al., "Protein localization in living cells and tissues using FRET and FLIM", Differentiation, 2003, vol. 71, pp. 528-541.
Dahan et al., "Diffusion Dynamics of Glycine Receptors Revealed by Single-Quantum Dot Tracking", Science, Oct. 17, 2003, vol. 302, pp. 442-445.
Day et al., "Imaging Molecular Interactions in Living Cells", Molecular Endocrinology, 2005, vol. 19, No. 7, pp. 1675-1686.
Denk et al., "Two-Photon Laser Scanning Fluorescence Microscopy", Reports, Apr. 6, 1990, pp. 73-76.
Dickson et al., "On/off blinking and switching behaviour of single molecules of green fluorescent protein", Nature, Jul. 24, 1997, vol. 388, pp. 355-358.
Ding et al., "Direct Observation of Protein Folding, Aggregation, and a Prion-like Conformation Conversion", Journal of Biological Chemistry, Dec. 2, 2005, vol. 280, No. 48, pp. 40235-40240.
Dobson, "The structural basis of protein folding and its links with human disease", Phil. Trans. R. Soc. Lond, 2001, vol. 356. pp. 133-145.
Dubertret et al., "In Vivo Imaging of Quantum Dots encapsulated in Phospholipid Micelles", Science, Nov. 29, 2002, vol. 298, pp. 1759-1762.
Empedocies et al., "Influence of Spectral Diffusions on the Line Shapes of Single CdSe Nanocrystallite Quantum Dots", J. Phys. Chem, 1999, vol. 103, pp. 1826-1830.
Giepmans et al., "The Fluorescent Toolbox for Assessing Protein Location and Function", Science, Apr. 14, 2006, vol. 312, pp. 214-224.
Gilmanshin et al., "Fast events in protein folding: Relaxation dynamics of secondary and tertiary structure in native apomyoglobin", Proc. natl. Acad. Sci. USA, Apr. 1997, vol. 94, pp. 3709-3713.
Greulich, "Fluorescense spectroscopy on single biomolecules", ChemPhysChem, 2005, vol. 6, pp. 2458-2471.
Hadjantonakis et al., "Technicolour Transgenics: Imaging Tools for Functional Genomics in the Mouse", Nature Reviews Genetics, Aug. 2003, vol. 4, pp. 613-627.
Hall, "Advanced sequencing technologies and their wider impact in microbiology", The Journal of Experimental Biology, 2007, vol. 209, pp. 1518-1525.
Harris et al., "Single-Molecule DNA Sequencing of a Viral Genome", Science, Apr. 4, 2008, vol. 320, pp. 106-109.
Hillier et al., "Whole-genome sequencing and variant discovery in *C. elegans*", Nature Methods, Feb. 2008, vol. 5, No. 2, pp. 183-188.
Jares-Erijman et al., "FRET imaging", Nature Biotechnology, Nov. 2003, vol. 21, No. 11, pp. 1387-1395.
Kim et al., "Mitochondrial permeability transition: a common pathway to necrosis and apoptosis", Biochemical and Biophysical Research Communications, 2003, vol. 304, pp. 463-470.
Kirson et al., "Alternating electric fields arrest cell proliferation in animal tumor models and human brain tumors", PNAS, Jun. 12, 2007, vol. 104, No. 24, pp. 10152-10157.
Lichtman et al, "Fluorescene microscopy", Nature Methods, Dec. 2005, vol. 2, No. 12, pp. 910-919.
International Search Report and Written Opinion for International Application No. PCT/US2012/066391, completed Feb. 23, 2013, 8 pgs.

International Search Report for International Application No. PCT/US07/085407 filed Nov. 21, 2007, Report completed Oct. 20, 2008, mailed Oct. 31, 2008, 2 pgs.
Written Opinion for International Application No. PCT/US2007/085407, filed Nov. 21, 2007, Opinion completed Oct. 20, 2008, mailed Oct. 31, 2007, 7 pgs.
Dombeck et al., "Optical Recording of Fast Neuronal Membrane Potential Transients in Acute Mammalian Brain Slices by Second-Harmonic Generation Microscopy", J. Neurophsiol. 2005, vol. 94, pp. 3628-3636.
Dworczak et al., "Electric field induced sescond harmonic generation (EFISH) experiments in the swivel cell: New aspects of an established method", Phys. Chem. Chem. Phys., 2000, vol. 2, pp. 5057-5064.
Franken et al., "Generation of Optical Harmonics", Physical Review Letters, Aug. 15, 1061, vol. 7, No. 4, pp. 118-120.
Girling et al., "Surface plasmon enhanced SHG from a hemicyanine monolayer", J. Phys. D: Appl. Phys, 1986, vol. 19, pp. 2065-2075.
Li et al., "Second harmonic generation in transparent KTiOPO4/SiO2 nanocomposite glasses prepared by the sol-gel method", Journal of Non-Crystalline Solids, 2000, vol. 261, pp. 273-276.
Loew, "Potentiometric dyes: Imaging electrical activity of cell membranes", Pure & Appl. Chem., 1996, vol. 88, No. 7, pp. 1405-1409.
Maiman, Stimulated Optical Radiation in Ruby, Nature, Aug. 6, 1960, vol. 187, pp. 493-494.
Peleg et al., "Nonlinear optical measurement of membrane potential around single molecules at selected cellular sites", Proc. Natl. Acad. Sci. USA, Jun. 1999, vol. 96, pp. 6700-6704.
Vogt et al., "Optical Second Harmonic Generation in Sodium Nitrite", phys. stat. sol. (a), 1970, vol. 1, pp. 439-450.
International Search Report for International Application No. PCT/US2007/085409, filed Nov. 21, 2007, Report completed Oct. 7, 2008, mailed Oct. 10, 2008, 2 pgs.
Akerman et al., "Nanocrystal targeting in vivo", PNAS, Oct. 1, 2002, vol. 99, No. 20, pp. 12617-12621.
Alivisatos, "The use of nanocrystals in biological detection", Nature Biotechnology, Jan. 2004, vol. 22, No. 1, pp. 47-52.
Andreoni et al., "Holographic properties of the second-harmonic cross correlation of object and reference optical wave fields", J. Opt. Soc. Am., Jun. 2000, vol. 17, No. 6, pp. 966-972.
Chalfie et al., "Green Fluorescent Protein as a Marker for Gene Expression", Science, New Series, Feb. 11, 1994, vol. 263, No. 5148, pp. 802-805.
Cuche et al., "Simultaneous amplitude-contrast and quantitative phase-contrast microscopy by numerical reconstruction of Fresnel off-axis holograms", Applied Optics, Dec. 1, 1999, vol. 38, No. 34, pp. 6994-7001.
Dobson, "Protein folding and misfolding", Nature, Dec. 18-25, 2003, vol. 426, pp. 884-890.
Dubois et al., "Improved three-dimensional imaging with a digital holography mircoscope with a source of partial spatial coherence", Applied Optics, Dec. 1, 1999, vol. 38, No. 34, pp. 7085-7094.
Gabor, "A New Microscopic Principle", Nature, May 15, 1948, No. 4098, pp. 777-778.
Gerlich et al., "4D imaging to assay complex dynamics in live specimens", Reviews, Sep. 2003, pp. S14-S19.
Jaiswal et al., "Use of quantum dots for live cell imaging", Nature Methods, Oct. 2004, vol. 1, No. 1, pp. 73-78.
Krenn et al., "Squeezing the Optical near-Field Zone by Plasmon Coupling of Metallic Nanoparticles", Physical Review Letters, Mar. 22, 1999, vol. 82, No. 12, pp. 2590-2593.
Kubelka et al., "The protein folding 'speed limit'", Current Opinion in Structural Biology, 2004, vol. 14, pp. 76-88.
Leith et al., "Microscopy of Wavefront Reconstruction", Journal of the Optical Society of America, Aug. 1965, vol. 55, No. 8, pp. 981-986.
Leith et al., "Wavefront Reconstruction with Diffused Illumination and Three-Dimensional Objects", Journal of the Optical Society of America, Nov. 1964, vol. 54, No. 11, pp. 1295-1301.
Maier et al., "Optical pulse propagation in metal nanoparticle chain waveguides", Physical Review, 2003, vol. B67, pp. 205402-1 thru 205402-5.

(56) References Cited

OTHER PUBLICATIONS

Maletic-Savatic et al., "Rapid Dendritic Morphogenesis in CA1 Hippocampal Dendrites Induced by Synaptic Activity", Science, Mar. 19, 1999, vol. 283, pp. 1923-1927.

Marquet et al., "Digital holographic microscopy: a noninvasive contrast imaging technique allowing quantitative visualization of living cells with subwavelength axial accuracy", Optics Letters, Mar. 1, 2005, vol. 30, No. 5, pp. 468-470.

Miccio et al, "Direct full compensation of the aberrations in quantitative phase microscopy of thin objects by a single digital hologram", Applied Physics Letters, 2007, vol. 90, pp. 041104-1 thru 041104-3.

Miyawaki et al., "Dynamic and quantitative Ca2+ measurements using improved cameleons", Proc. Natl. Acad. Sci. USA, Mar. 1999, vol. 96, pp. 2135-2140.

Pedrini et al., "Aberration compensation in digital holographic reconstruction of microscopic objects", Journal of Modern Optics, 2001, vol. 48, No. 6, pp. 1035-1041.

Pollok et al., "Using GFP in FRET-based applications", Trends in Cell Biology, Feb. 1999, vol. 9, pp. 57-60.

Pu et al., "Four-dimensional dynamic flow measurement by holographic particle image velocimetry", Applied Optics, Dec. 20, 2005, vol. 44, No. 36, 7697-7708.

Pu et al., "Intrinsic aberrations due to Mie scattering in particle holography", J. Opt. Soc. Am, Oct. 2003, vol. 20, No. 10, pp. 1920-1932.

Qiu et al., "Conducting Polyaniline Nanotubes by Template-Free Polymerization", Macromolecules, 2001, vol. 34, pp. 675-677.

Schnars et al., "Direct recording of holograms by a CCD target and numerical reconstruction", Applied Optics, Jan. 19, 1994, vol. 33, No. 2, pp. 179-181.

Shi et al., "Rapid Spine Delivery and Redistribution of AMPA Receptors After Synaptic Nmda Receptor Activation", Science, Jun. 11, 1999, vol. 284, pp. 1811-1816.

Toth et al., "Reconstruction of a Three-Dimensional Microscopic Sample Using Holographic Techniques", Applied Physics Letters, Jul. 1, 1968, vol. 13 No. 1, p. 7-9.

Xu et al., "Tracking particles in four dimensions with in-line holographic microscopy", Optics Letters, Feb. 1, 2003, vol. 28, No. 3, pp. 164-166.

Yamaguchi et al., "Phase-shifting digital holography", Optics Letters, Aug. 15, 1997, vol. 22, No. 16, pp. 1268-1270.

Zhang et al., "Three-dimensional microscopy with phase-shifting digital holography", Optics Letters, Aug. 1, 1998, vol. 23, No. 15, pp. 1221-1223.

Zipfel et al., "Nonlinear magic: multiphoton microscopy in the biosciences", Nature Biotechnology, Nov. 2003, vol. 21, No. 11, pp. 1369-1377.

Chang et al., "An Efficient Approach to Derive Hydroxyl Groups on the Surface of Barium Titanate Nanoparticles to Improves tis Chemical Modification Ability", Journal of Colloid and Interface Science, 2009, pp. 300-305.

Cohen, "Beyond fluorescence", Nature, Sep. 23, 2010, vol. 467, pp. 407-408.

Sandrock et al., "Synthesis and Second-Harmonic Generation Studies of Noncentrosymmetric Gold Nanostructures", J. Phys. Chem. B, 1999, vol. 103, pp. 2668-2673.

Shalaev, "Electromagnetic Properties of Small-Particle Composites", Physics Reports, 1996, 272, pp. 61-137.

Williams et al., "Fast Events in Protein Folding: Helix Melting and Formation in a Small Peptide", Biochemistry, 1996, vol. 35, pp. 691-697.

Zayats et al., "Second-harmonic generation from individual surface defects under local excitation", Physical Review B, Feb. 15, 2000, vol. 61, No. 7, pp. 4545-4548.

* cited by examiner

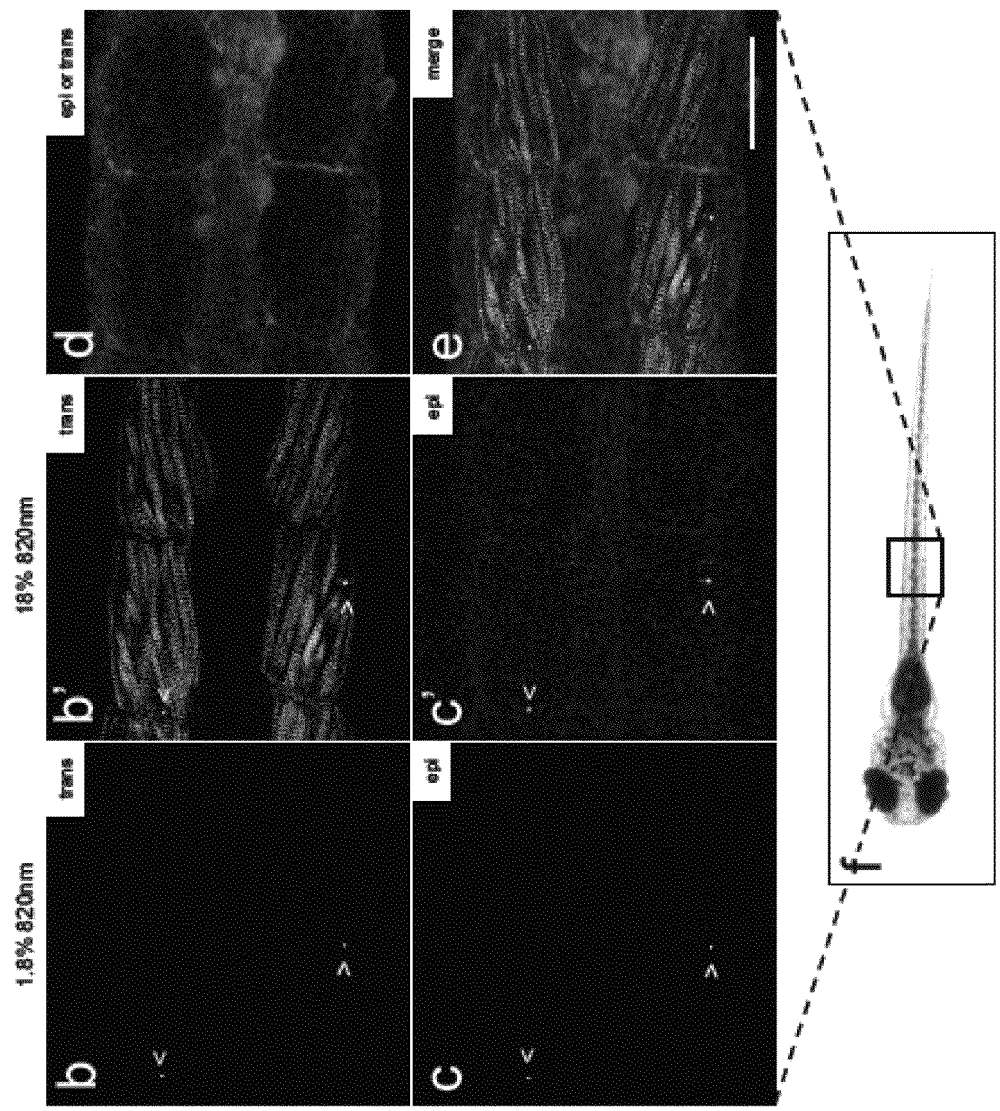
FIG. 2b-f

US 8,945,471 B2

MULTIPURPOSE ANALYSIS USING SECOND HARMONIC GENERATING NANOPROBES

CROSS REFERENCE TO RELATED APPLICATIONS

The current application claims priority to U.S. Provisional. Application Nos. 61/205,488, filed Jan. 21, 2009 and 61/206,960, filed Feb. 6, 2009, the disclosures of which are incorporated herein by reference.

STATEMENT OF FEDERAL SUPPORT

The U.S. Government has certain rights in this invention pursuant to Grant Nos. Grant No(s). HD043897 and HGD04071 awarded by the National Institutes of Health.

FIELD OF THE INVENTION

The current invention is directed second harmonic generating nanoprobes and methodologies of imaging and analyzing a variety of structures and processes using second harmonic generating nanoprobes.

BACKGROUND OF THE INVENTION

One of the grand open challenges in modern science is to image or monitor processes or structures that are very small and operate at a fast time-scale. For example, it is extremely difficult to identify cells or probe molecules and understand the mechanism and dynamics of biological processes at the molecular level with high sensitivity and spatiotemporal resolution, and particularly inside living cells and tissue or liquid. As a result of the wealth of information potentially accessible from such biological targets, there has been a growing demand for imaging tools for biomedical research and medicine. In addition, the continued miniaturization of integrated circuits has led to increasingly small devices. As the distances between components have shrunk, the electric fields generated by these components have increased. These larger electric fields carry the added risk that an electrical short or breakdown effect will occur somewhere in the circuit. If a circuit does not perform to specification, locating troublesome areas can be stymied by the complexity of modern-day circuits; checking each node of the circuit is time-consuming and technically difficult. Accordingly, a need exists to optically measure abnormalities in electric field.

These issues have led to the development of new techniques like magnetic resonance imaging (MRI), ultrasound, positron emission tomography (PET), and optical coherence tomography (OCT). However, these techniques require high costs and some fundamental technological barriers hinder their widespread use.

Optical imaging is a recent technique that utilizes photons as an information source with applications in a wide range of basic science and clinical studies like pharmacology, cellular biology, and diagnostics. For example, semiconductor nanocrystals, small organic dyes or fluorescent proteins are commonly used as optical labels in in vivo optical imaging. (See, e.g., X. Michalet et al., Science 307, 538 (Jan. 28, 2005); B. Dubertret et al., Science 298, 1759 (Nov. 29, 2002); M. K. So, C. Xu, A. M. Loening, S. S. Gambhir, J. Rao, Nat Biotechnol 24, 339 (March, 2006); N. C. Shaner, P. A. Steinbach, R. Y. Tsien, Nat Methods 2, 905 (December, 2005); and B. N. Giepmans, S. R. Adams, M. H. Ellisman, R. Y. Tsien, Science 312, 217 (Apr. 14, 2006), the disclosures of which are incorporated herein by reference.) Moreover, recent advances in fluorescence microscopy alone have profoundly changed how cell and molecular biology is studied in almost every aspect. (For example, see, Lichtman, J. W. & Conchello, J. A. Nat. Methods 2, 910-919 (2005); Michalet, X. et al. Annu. Rev. Biophys. Biomolec. Struct. 32, 161-182 (2003); Jares-Erijman, E. A. & Jovin, T. M. Nat. Biotechnol. 21, 1387-1395 (2003); Bastiaens, P. I. H. & Squire, A., Trends Cell Biol. 9, 48-52 (1999); and Suhling, K., et al., Photochem. Photobiol. Sci. 4, 13-22 (2005), the disclosures of which are incorporated herein by reference.) Indeed, since the cloning of the green fluorescent protein (GFP) from the jellyfish *Aequorea victoria* a large variety of genetically encoded fluorescent tags have come to be used in in vivo optical imaging. (See, e.g., Prasher, D. C., et al., Gene 111, 229-233 (1992); and Shaner, N. C., et al., Nat Methods 2, 905-909 (2005), the disclosures of each of which are incorporated herein by reference.) They have proven to be particularly important in analyzing a variety of biological processes such as gene expression, and the localization and dynamics of fluorescent-tagged proteins or fluorescent marked cell populations. (See, e.g., Lippincott-Schwartz, J., et al., Nat Rev Mol Cell Biol 2, 444-456 (2001); and Hadjantonakis, A. K., et al., Nat Rev Genet. 4, 613-625 (2003), the disclosures of each of which are incorporated herein by reference.)

However, the ultimate need of characterizing biological targets is largely unmet due to fundamental deficiencies associated with the use of fluorescent agents. For example, fluorescent probes face two major limitations that have a significant impact on the signal strength: 1) dye saturation, because the number of photons emitted by the fluorophore in a given time is restricted by the excited state lifetime, and 2) dye bleaching, which limits the total number of photons per dye. Among these problems, bleaching is perhaps the most significant issue in the application of fluorescent probes, limiting significantly the length of time that biological targets can be studied. In particular, directly tracking the lineage of distinct cell populations in tissue or monitoring the dynamics of molecules within single cells depend critically on long-term photostability. In addition, autofluorescence from tissue organic components due to illumination absorption can severely limit the signal-to-noise ratio. Finally, fluorescence is fundamentally an optically incoherent process, and as a result extracting 3D information from the source is inherently difficult.

Accordingly, a need exists for a new probe for imaging/detecting biological structures and processes that avoids the inherent technological limitations found in the fluorescent imaging techniques of the prior art.

SUMMARY OF THE INVENTION

The current invention is directed to nanoprobes for multi-purpose imaging/detecting based on a novel second harmonic generating (SHG) technique.

In one embodiment, the probe nanostructures—referred to as SHG nanoprobes—that generate second harmonic signals emit coherent waves for imaging targets without bleaching, blinking or saturation.

In another embodiment, the probes of the current invention are formed of two dissimilar types of nanostructures: a first exciter nanostructure that resonates at the frequency of the pump, and a second probe nanostructure that generates second harmonic signals (SHG nanoprobe).

In still another embodiment, the first exciter nanostructure is a metal nanostructure and the second probe nanostructure is nanocrystals, the SHG nanoprobes.

In yet another embodiment, the exciter nanostructure is chosen such that when pumped via a continuous wave, modulated or pump source it enhances the electric field within a few nanometers of its vicinity. In such an embodiment, the enhanced local field can couple with neighboring SHG nanoprobe, and the short-range interactions can then be used as a nanometer sensitive distance gauge.

In still yet another embodiment, the current invention is directed to a method of imaging/detecting with superb sensitivity and spatiotemporal resolution biological process and structures using a field resonance enhanced second harmonic (FRESH) technique.

In still yet another embodiment, the current invention is directed to a method of using the SHG nanoprobes in a nucleotide detection scheme. In such an embodiment, a distinct probe nanostructure is attached to each distinct nucleotide of interest. Alternatively, this method of nucleotide detection can be combined with superb sensitivity and spatiotemporal resolution biological process and structures using a field resonance enhanced second harmonic (FRESH) technique.

In still yet another embodiment, the current invention is directed to a voltage sensitive SHG nanoprobe—referred to as VS-SHG nanoprobes. In such an embodiment, the VS-SHG nanoprobe is designed to monitor the electric field generated by a target species or device. In one such embodiment, the voltage sensitive VS-SHG nanoprobe is designed to detect/evaluate a (physiologically generated) electric field.

BRIEF DESCRIPTION OF THE DRAWINGS

The description and claims of the current invention will be more fully understood with reference to the following figures and data graphs, which are presented as exemplary embodiments of the invention and should not be construed as a complete recitation of the scope of the invention, wherein:

FIGS. 2a to 2f provide photographs exhibiting the in vivo imaging properties of an exemplary SHG nanoprobe in accordance with the current invention;

DETAILED DESCRIPTION OF THE INVENTION

The current invention is generally directed to a methodology for imaging/detecting targets of interest using nanoprobes capable of producing a second harmonic generation response; referred to from hereinafter as SHG nanoprobes. In addition, the application is directed to a technique for dynamic imaging/detecting dynamic processes like molecule conformation changes or molecule-molecule interactions using a field resonance enhanced second harmonic technique; referred to from hereinafter as FRESH. The invention is also directed to a technique for imaging nucleotide sequencing using a Multi-SHG Detection Imaging (MSDI) modality. Finally, the invention is directed to voltage-sensitive SHG nanoprobes capable of monitoring electric fields; referred to from hereinafter as VS-SHG nanoprobes. All the imaging techniques are designed to overcome the shortcomings of conventional fluorescence-based techniques.

Specifically, to overcome the limitations inherent in conventional imaging techniques, the current invention is drawn to an imaging methodology that uses second harmonic generating (SHG) nanoprobes that are suitable for multipurpose imaging/detecting (including in vivo/in vitro) and can avoid most of the inherent drawbacks encountered in classical optical systems. The operation of this invention is based on labeling molecules, cells, nucleotides or other targets of interest with nonlinear materials having very distinctive emissive characteristics, e.g., various kinds of inorganic and/or organic nanocrystals (and a combination of them) that do not possess an inversion symmetry, and therefore are capable of generating second harmonic signals.

Figure 1A:
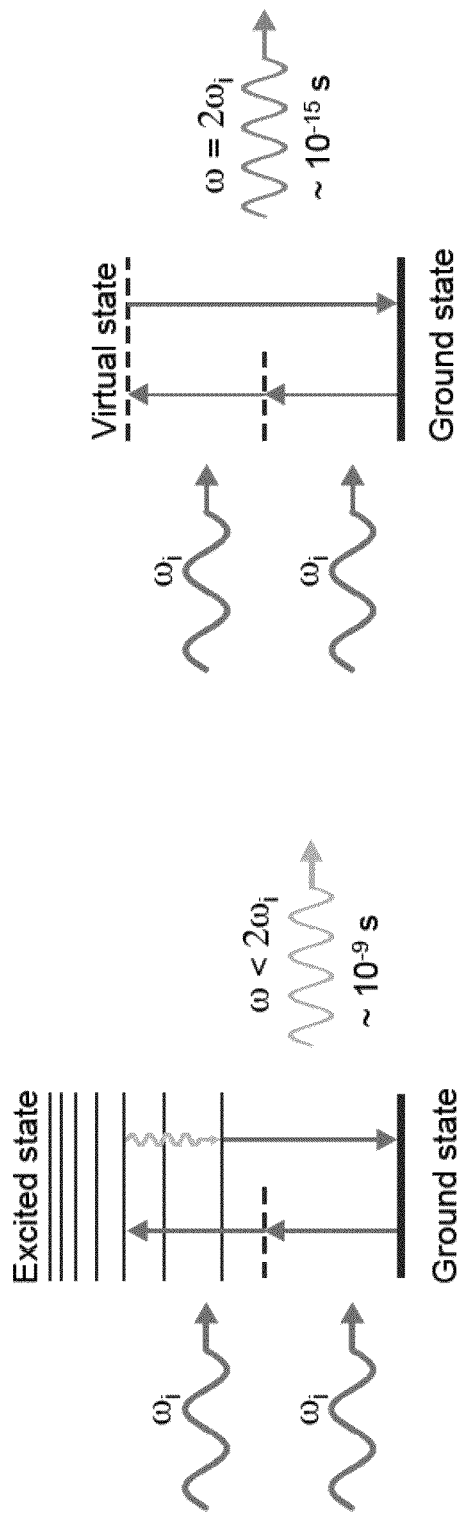
FIG. 1a provides a schematic diagram comparing the properties of the second harmonic technique of the current invention with the fluorescence used in conventional optical systems.

SHG microscopy is an emerging microscopic technique for a wide range of imaging applications. In summary, SHG is a second-order nonlinear optical process in which two photons at the frequency (ω) interacting with non-centrosymmetrical media (i.e. material lacking a generalized mirror symmetry) are combined to form a new photon with twice the energy, and therefore twice the frequency (2ω) and half the wavelength of the initial photons. (See, e.g., Boyd, R. W., Nonlinear optics, 2nd Edition, (San Diego, Calif.: Academic Press) (2003); and Sutherland, R. L., et al., Handbook of nonlinear optics, 2nd Edition, (New York: Marcel Dekker) (2003), the disclosures of each of which are incorporated herein by reference.) This process is shown diagrammatically in FIG. 1a. The optical response of the media can be described by expressing the induced polarization P(ω) as a power series of the optical field strength E(ω) of the incident light:

$$P(\omega)=\chi^{(1)} \cdot E(\omega)+\chi^{(2)} \cdot E(\omega)^2+\chi^{(3)} \cdot E(\omega)^3+ \quad \text{(Eq. 1)}$$

Where the coefficient $\chi^{(n)}$ is the $\chi^{th}$-order susceptibility of the material, $\chi^{(1)}$, $\chi^{(2)}$, and $\chi^{(3)}$ corresponding to optical effects such as absorption or reflection, second harmonic generation (SHG), and third harmonic generation, respectively.

With such symmetry constraints SHG can be mainly produced from structures without inversion symmetry combined with a high degree of organization and orientation, such as anisotropic crystals or endogenous structural protein arrays in tissue. Using SHG microscopy, a variety of tissue structures have been imaged non-invasively by virtue of the intrinsic signal generated by structured proteins such as collagen fibrils in connective tissues or the actomyosin lattice of muscle cells. (See, e.g., Campagnola, P. J., and Loew, L. M. Nat Biotechnol 21, 1356-1360 (2003), the disclosure of which is incorporated herein by reference.) For typical tissue such emissions might range, for example, from 350 to 700 nm, although other wavelengths might be used dependent on the material to be imaged. These emissions can then be detected by any optical based technique, such as, for example, conventional two-photon microscopy (for example, for wavelengths in the range of 350 to 700 nm by tuning the wavelength from 700 to 1400 nm), or continuous wave, modulated, or other pulsed lasers having for example nano, pico, femto, or attosecond timeframes.

As a nonlinear optical process, SHG shares many features with two-photon excited fluorescence. Using pulsed lasers in the infrared wavelength range it offers deeper optical penetration and reduced nonspecific phototoxicity compared to one-photon excitation. (See, e.g., Pantazis, P., and Gonzalez-Gaitan, M. J Biomed Opt 12, 044004 (2007), the disclosure of which is incorporated herein by reference.) These properties are of vital importance for long time-lapse imaging. However, two-photon excited fluorescence relies on nonlinear absorption by a dye that can bleach and/or generate toxic by-products; in contrast, SHG is a coherent process involving only virtual energy transitions. As a result, photodamage is significantly limited, since SHG does not arise from an absorptive process.

Second harmonic generation has many inherent advantages over fluorescence that open the possibility of a wide variety of applications. These advantages are discussed with reference to the Perrin-Jablonski fluorescence diagram (left) and the energy-level diagram (right) describing two-photon excited fluorescence and SHG, respectively provided in FIG. 1a. In short, when intense light is shone on materials that do not possess an inversion symmetry, the vibrating electric field of the incident beam results in the polarization of the medium, re-emitting light at the original frequency $\omega_i$ but also at the frequency $2\omega_i$ (here shown, right) that is twice the original one (with half of the wavelength).

First, unlike two-photon excited fluorescence, all of the incident radiation power at frequency $w_i$ is converted in the process of SHG to radiation at the SHG frequency $2\omega_i$.

Second, as a parametric nonlinear optical process, second harmonic generation does not involve real electron energy transition but only virtual transitions. Fluorescence, on the other hand, involves actual energy transition of electrons. As a result, the response time of second harmonic generation is instantaneous and is only limited by the excitation and detection speed. For example using a femtosecond pulsed laser the response time is at the femtosecond level, about four to five orders of magnitude faster than the nanosecond response time of fluorescence, allowing very fast and sensitive detection of molecules with appropriate detection systems. (See, e.g., R. W. Boyd, Nonlinear optics (Academic Press, San Diego, Calif., ed. 2nd, 2003), pp. xvii, 578 p, the disclosure of which is incorporated herein by reference.)

Third, biological tissue does not often assemble into large, ordered noncentrosymmetric structures. As a result, biological tissue does not generate a strong SHG signal, therefore, the SHG nanoprobes can be imaged with sharp contrast (high signal-to-noise ratio) when presenting in vivo, allowing detection of single SHG nanoprobes attached to molecules of interest or identification of cells of interest harboring an SHG nanoprobe in tissue.

Figure 1B:
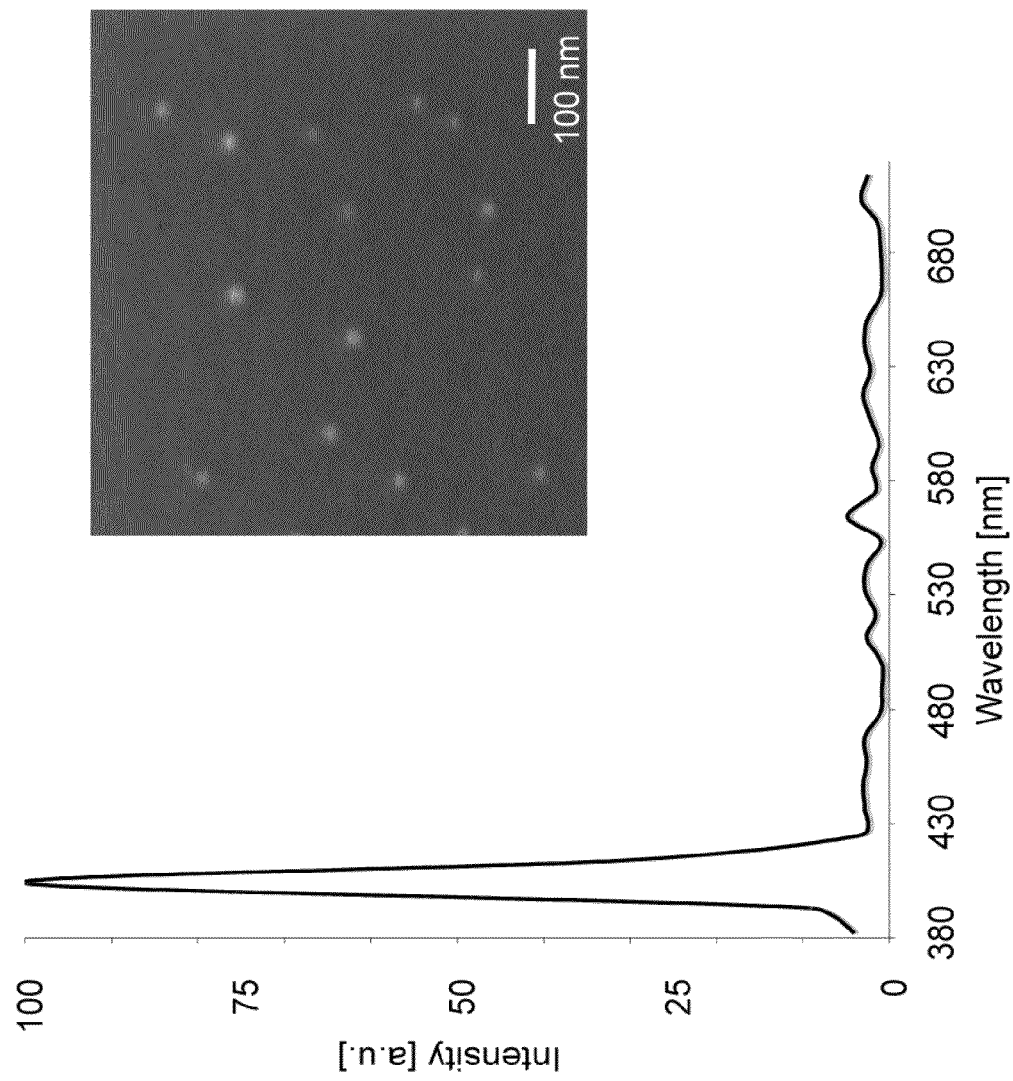
FIGS. 1b to 1d provide data plots of the emission profile of an exemplary SHG nanoprobe in accordance with the current invention (b), data graphs showing the absence of bleaching and blinking for an exemplary SHG nanoprobe in accordance with the current invention (c), and data graphs showing the saturation properties for an exemplary SHG nanoprobe in accordance with the current invention and a conventional quantum dot (d)
Figure 1C:
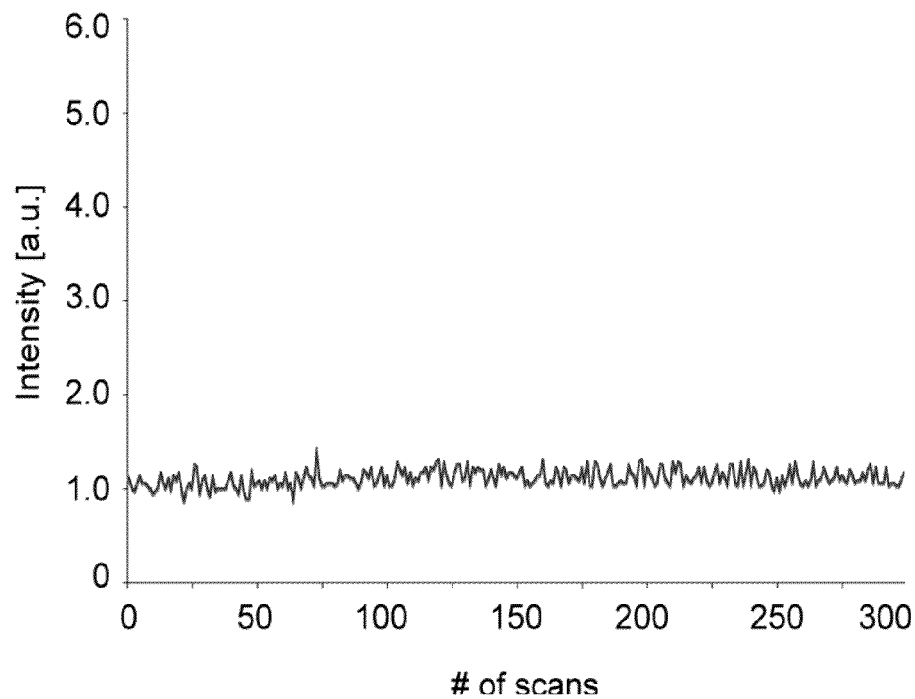

Fourth, unlike fluorescent dyes, SHG nanoprobes do not undergo photo-bleaching or blinking, as shown in FIG. 1c. In this set of data graphs, single $BaTiO_3$ nanocrystals were immobilized in 20% polyacrylamide and illuminated with 820 nm light 300 times with a scanning speed of 20 frames per second. As shown, in contrast to conventional quantum dots (QDs) whose signal fluctuates displaying blinking and photobleaching, the second harmonic signal intensity of SHG nanoprobes made of $BaTiO_3$ is constant, making it a superior single molecule detection probe. (See, e.g., W. Denk, J. H. Strickler, W. W. Webb, Science 248, 73 (Apr. 6, 1990), the disclosure of which is incorporated herein by reference.)

Figure 1D:
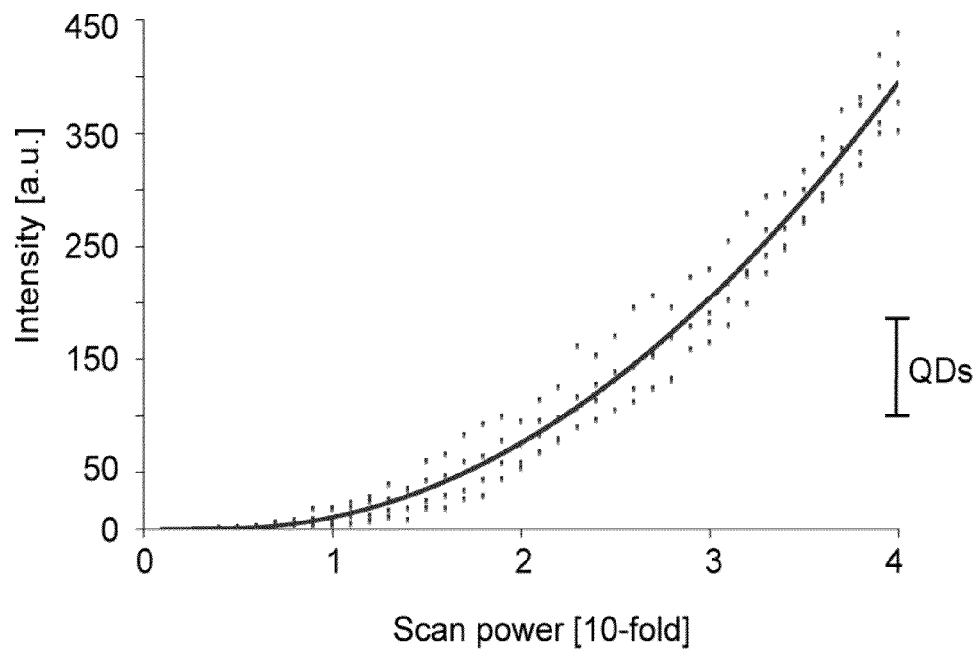

Fifth, again unlike fluorescent dyes, SHG nanoprobes do not undergo photo-saturation with increasing illumination intensity, as shown in FIG. 1d. In this set of data graphs, $BaTiO_3$ nanocrystals and water-soluble CdSe/ZnS quantum dots (QD) were immobilized in 20% polyacrylamide and illuminated with increasing 820 nm light intensity. As shown, signal saturation of QD occurs already at very low power levels with a small intensity range, whereas the second harmonic signal of $BaTiO_3$ SHG nanoprobes increases quadratically, allowing very efficient visualization or detection of, for example, a single molecule attached to such as a SHG nanoprobe, for example, in tissue or sample solution by simply increasing the illumination power. (See, e.g., C. K. Sun, Adv Biochem Eng Biotechnol 95, 17 (2005), the disclosure of which is incorporated herein by reference.)

Finally, the SHG nanoprobes of the current invention show a high pH stability allowing targeting a wider range of molecules of interest, such as, for example, acidic organelles without signal loss. The biocompatibility of the technique was also studied, and it has been shown that injected embryos developed indistinguishably from uninjected counterparts.

As discussed above, the basic principle behind the SHG nanoprobes of the current invention is to attach to a target or device of interest a probe nanostructure that generates a second harmonic signal or to identify cells or tissue of a living subject (in vivo/in vitro) using such SHG nanoprobes. Such a structure may be any organic, inorganic or combination of organic and inorganic nanocrystal, such as, for example $BaTiO_3$, SiC, ZnO, ZnS, ZnSe, ZnTe, CdS, CdSe, CdTe, GaAs, GaSb, GaP, GaN, InSb, $LiNbO_3$, $KNbO_3$, $KTiOPO_4$, Fe(IO$_3$)$_3$, Au, Ag, N-(4-nitrophenyl)-(L)-prolinol (NPP), urea, 4-Nitroaniline, 2-Methyl-4-nitroaniline (MNA), 3-Methyl-4-methoxy-4'-nitrostilbene), β-BaB2O4 (Beta-Barium Borate/BBO, LiB3O5 (Lithium Triborate/LBO), LiNbO3 (Lithium Niobate/LN), KTiOPO4 (Potassium Titanyl Phosphate/KTP), AgGaS2 (Silver Thiogallate/AGS), AgGaSe2 (Silver Gallium Selenide/AGSe), ZnGeP2 (Zinc Germanium Phosphide/ZGP), GaSe (Gallium Selenide), KH2PO4 (Potassium Dihydrogen Phosphate/KDP), NH4H2PO4 (Ammonium Dihydrogen Phosphate (ADP), KD2PO4 (Deuterated Potassium Dihydrogen Phosphate/DKDP), CsLiB6O10 (Cesium Lithium Borate/CLBO), KTiOAsO4 (Potassium Titanyl Arsenate/KTA), KNbO3 (Potassium Niobate/KN), LiTaO3 (Lithium Tantalate/LT), RbTiOAsO4 (Rubidium Titanyl Arsenate/RTA), BaTiO3 (Barium Titanate), MgBaF4 (Magnesium Barium Fluoride), GaAs (Gallium Arsenide), BiB3O6 (Bismuth Triborate/BIBO), K2Al2B2O7 (Potassium Aluminum Borate/KABO), KBe2BO3F2 (Potassium Fluoroboratoberyllate/KBBF), BaAlBO3F2 (Barium Aluminum Fluoroborate/BABF), La2CaB10O19 (Lanthanum Calcium Borate/LCB), GdCa4O(BO3)3 (Gadolinium Calcium Oxyborate/GdCOB), YCa4O(BO3)3 (Yttrium Calcium Oxyborate/YCOB), Li2B4O7 (Lithium Tetraborate/LB4), LiRbB4O7 (Lithium Rubidium Tetraborate/LRB4), CdHg (SCN)4 (Cadmium Mercury Thiocyanate/CMTC), RbTiOPO4 (Rubidium Titanyl Phosphate/RTP), LiInS2 (Lithium Thioindate/LIS), LiInSe2 (Lithium Indium Selenide/LISe), KB5O8.4H2O (Potassium Pentaborate Tetrahydrate/KB5), CsB3O5 (Cesium Triborate/CBO), C4H7D12N4PO7 (Deuterated L-Arginine Phosphate Monohydrate/DLAP), a-HIO3 (a-Iodic Acid), LiCOOH.H2O (Lithium Formate Monohydrate/LFM), CsH2AsO4 (Cesium Dihydrogen Arsenate/CDA), CsD2AsO4 (Deuterated Cesium Dihydrogen Arsenate/DCDA), RbH2PO4 (Rubidium Dihydrogen Phosphate/RDP), CsTiOAsO4 (Cesium Titanyl Arsenate/CTA), Ba2NaNb5O15 (Barium Sodium Niobate/BNN), K3Li2Nb5O15 (Potassium Lithium Niobate/KLN), CO(NH2)2 (Urea), LiIO3 (Lithium Iodate), Ag3AsS3 (Proustite), HgGa2S4 (Mercury Thiogallate), CdGeAs2 (Cadmium Germanium Arsenide/CGA), Ti3AsSe3 (Thallium Arsenic Selenide/TAS), CdSe (Cadmium Selenide), ZnO (Zinc Oxide), ZnS (Zinc Sulfide), ZnSe (Zinc Selenide), ZnTe (Zinc Telluride), CdS (Cadmium Sulfide), SiC (Silicon Carbide), and GaN (Gallium Nitride), GaSb (Gallium Antimonide), among others. In addition, the SHG nanoprobes may include magneto-SHG particles, such as, for example, ferromagnetic, ferrimagnetic, paramagnetic, diamagnetic, superparamagnetic (i.e., Fe3O4), superdiamagnetic, and metamagentic superparamagnetic material as well as resonant material nanoshells around the SHG nanoprobe particles such as, for example, gold, silver, copper, aluminum, palladium, or platinum.

In one further embodiment, the above SHG nanoprobes may be further functionalized to provide the targeting and delivery characteristics necessary for the nanoprobe to attach to a desired target molecule. Functionalization may be provided by introducing functional groups on the surface of SHG nanoprobes, including, but are not limited to: sulfhydryl residues, carboxylate groups, primary amine groups, aldehyde residues, and hydrazide functional groups. The targeting may be made by cross-linking reagents, including, but are not limited to: zero-length cross-linkers (among them Carbodiimides), homobifunctional cross-linkers (among them NHS esters, imidoesters), heterobifunctional cross-linkers (among them amine-reactive and sulfhydryl-reactive cross-linkers), and trifunctional cross-linkers (among them sulfo-SBED). In one particular embodiment, the SHG nanoprobes may be modified or functionalized with a synthetic polymer, the free ends of which may be further modified. In one such embodiment, the SHG nanoprobes may be PEGylated and the ends not used for coupling to the particle surface may be made active to various (bio-active) species (protein, DNA, RNA or non-biological material) by (covalent) coupling by a number PEG analogues, including: biotin, bromo, amino, aminoethyl, carboxymethyl, succinimidosuccinate, tosylate, mesylate, aldehyde, actadecylamine, monopalmitate, stearoyloxy derivatives of PEG. Example 6, below, provides an exemplary strategy for the functionalization of an SHG nanoprobe (BaTiO$_3$) including the surface modification of this entity with synthetic polymers (to afford long-circulating properties) and to targeting ligands for selective attachment at desired sites.

Although a few specific examples of possible SHG nanoprobes are described above, it should be understood that any nanostructure, defined hereinafter as a structure of ≤10 μm, capable of second harmonic generation may be used in the current invention. The requirement of the materials, as discussed above, being that the nanostructure not possess an inversion symmetry center.

It should be understood that the SHG nanoprobes of the current invention may be used with a wide variety of targets of interest such as, for example, proteins, DNA, RNA, cells, tissue or non-biological material. If the molecule of interest is a cell, such a cell may be, for example, a cancer cell, stem cell, or tumor.

Although only single types of SHG nanoprobes are discussed above, it should be understood that a plurality of SHG nanoprobes displaying distinct emission profiles can be used to identify various labeled molecules or cells of interest in parallel. Although one exemplary excitation profile generated through standard two-photon excitation is provided in Example 1, below, it should be understood that any conventional excitation source may be used that is compatible with second harmonic generation.

Although only specific embodiments of the invention are discussed above and in the examples below, it should be understood that the unique combination of properties possessed by the second harmonic nanoprobes of the current invention allows for a number of applications including, for example, nucleotide imaging for sequencing, protein, DNA, RNA and tumor imaging and cancer or stem cell therapy evaluation and diagnosis as well as quantification in optical imaging, (in vivo/in vitro) imaging of biological processes such as cell signaling, neuroimaging, protein conformation probing, DNA conformation probing, gene transcription, and virus infection and replication in cells. In addition the SHG nanoprobes of the current invention may be used to for a number of (in vivo/in vitro/in silico) imaging applications.

For example, as will be discussed in greater detail below, the SHG nanoprobes may be used to develop electric field maps for electronics such as integrated circuits.

Exemplary Embodiments

The present invention will now be illustrated by way of the following examples, which are exemplary in nature and are not to be considered to limit the scope of the invention.

EXAMPLE 1

SHG Nanoprobe Emission Profiling

FIGS. 1b to 1d provide exemplary data graph for a second harmonic emission profile generated from BaTiO$_3$-nanocrystals in accordance with the current invention, and in comparison to the emission characteristics of conventional. Quantum Dots (QD) (d). As shown, the second harmonic emission ranges from 380 to 485 nm displaying, unlike many other optical probes, discrete emission peaks of around 10 nm, and was generated by conventional two-photon excitation, where the excitation energy ranges from 760 to 970 nm.

For this data (spectrum, blinking property comparison, and signal saturation comparison) SHG nanomaterial solutions were ultrasonicated, nanofiltered and immobilized in 20% polyacrylamide gel. The spectrum was analyzed with the Meta detector of the Zeiss 510NLO microscope setup. For the blinking property comparison between $BaTiO_3$ and water-soluble QD, both immobilized nanomaterials were imaged 300 times (20 frames/second) using a 40×/1.3 oil objective on a Zeiss 510NLO microscope setup. A mode-locked infrared laser line at 820 nm was used, originating from a two photon Ti::Sapphire laser (Coherent Inc.). The background value was set to 0 and each obtained dataset was normalized accordingly. Data were analyzed using the Zeiss LSM software.

For the signal saturation comparison between $BaTiO_3$ and water-soluble QD, both immobilized nanomaterials were illuminated rapidly 5 times each (in particular to minimize fluctuating intensity values for blinking QDs) with increasing (up to 40 fold) 820 nm light intensity (n=4). Data of nanocrystals and QDs having intensity values within the optimal photomultiplier gain setting were recorded and analyzed using the Zeiss LSM software.

Specifically, FIG. 1b provides a data plot displaying the normalized SHG signal spectrum of $BaTiO_3$ nanocrystals of the size of around 30 nm (inset: scanning electron microscope (SEM) picture of $BaTiO_3$ nanocrystals) immobilized in 20% polyacrylamide gel. (signal ranging from 380 to 710 nm) generated by tuning the excitation wavelength to 820 nm. FIG. 1b shows the SHG signal profile from $BaTiO_3$ nanocrystals of the size of around 30 nm (FIG. 1b inset) covering the spectral range from 380 to 720 nm when excited with a conventional two-photon microscope, tuning the illumination wavelength to 820 nm. The SHG signal profile displays a high SNR with a discrete peak at 410 nm. The peak full width at half maximum (FWHM), which can be directly deduced from the fact that the SHG frequency bandwidth scales as $1/\sqrt{2}$ of that of the incident laser, is around 5 nm. This FWHM is narrower than of those in biomedical imaging commonly used quantum dots (QDs) as well as significantly narrower than of the recently introduced non-blinking quantum dots, which display a very broad, multi-peaked spectrum. (See, e.g., Bruchez, M., Jr., et al., *Science* 281, 2013-2016 (1998); Chan, W. C., and Nie, S., *Science* 281, 2016-2018 (1998); and Wang, X., et al., *Nature* 459, 686-689 (2009), the disclosures of which are incorporated herein by reference.) With these spectral properties, optimized emission filters can be employed with precise, very narrow bandwidths excluding longer wavelengths, which can block most endogenous autofluorescence from random tissue absorption (see below). The signal properties remained stable over several hours and in various organic solvents (e.g. methanol, toluene) or concentrated salts (0.1-2.0 M).

A major interest in biological imaging is to detect, identify and track individual molecules in biological systems with high spatial resolution and in physiological conditions. One important limitation of using QDs with proven records in aqueous solubilization, and biomolecular conjugation to track individual target molecules results from 'blinking', the intrinsic fluorescence intermittency of QDs, which has been reported for single fluorescent molecules as well. (See, e.g., Dickson, R. M., et al., *Nature* 388, 355-358 (1997), the disclosure of which is incorporated herein by reference.) Long random blinking intervals, alternation of periods when the QD emits fluorescence photons or when it is dark, do not allow continuous tracking of individual molecule trajectories, complicating considerably the data analysis. (See, e.g., Pelton, M., Smith, G., Scherer, N. F., and Marcus, R. A., *Proc Natl Acad Sci USA* 104, 14249-14254 (2007); and Dahan, M., et al., *Science* 302, 442-445 (2003), the disclosures of each of which are incorporated herein by reference.)

FIG. 1c provides a data plot showing that fast time-lapse sequences of immobilized $BaTiO_3$ nanocrystals in 20% polyacrylamide gel do not demonstrate blinking behavior. In particular, FIG. 1c, provides a data plot of $BaTiO_3$ nanocrystal immobilized in 20% polyacrylamide gel and illuminated with low intensity levels of 820 nm light 300 times with a scanning speed of 20 frames per second. As shown, the SHG signal intensity of $BaTiO_3$ is constant and does not display blinking. Because SHG involves only virtual energy transitions, the SHG nanoprobes do not directly absorb energy, causing the signal intensity to stay unchanged when successively recorded 300 times within 15 seconds. In addition, the SHG signal remains constant over much longer time periods (data not shown). In contrast, immobilized QDs demonstrate pronounced blinking behavior with large fluorescence intensity changes between the on and off states, as has been extensively described in prior studies. (See, e.g., Nirmal, M., et al., *Nature* 383, 802-804 (1996); Basche, T., *Journal of Luminescence* 76-77, 263-269 (1998); and Empedocles, S. A., *Journal of Physical Chemistry B* 103, 1826 (1999), the disclosures of each of which are incorporated herein by reference.)

As previously discussed, two limiting features when distinguishing a low abundance molecular target are sensitivity and rapidity of acquisition. Common fluorescent probes (e.g. organic dyes or GFP) used as molecular reporters have two major disadvantages: dye saturation and dye bleaching, which ultimately result in poor SNR. QD-based molecular tracking has significantly enhanced the detection limit due to its increased quantum yield and enhanced photostability. However, QD dye saturation limits the SNR in a given time frame. (See, e.g., Michler, P., et al., *Nature* 406, 968-970 (2000), the disclosure of which is incorporated herein by reference.) Likewise, this limitation applies to the recently introduced non-blinking quantum dots. (See, e.g., Wang, X., et al., *Nature* 459, 686-689 (2009), the disclosure of which is incorporated herein by reference.) To improve the signal, long integration times must be used, sacrificing temporal resolution. (See, e.g., Bannai, H., et al., *Nat Protoc* 1, 2628-2634 (2006), the disclosure of which is incorporated herein by reference.) To compare the achievable signal intensities of SHG nanoprobes to QDs when imaged rapidly, the illumination intensity shone on $BaTiO_3$ nanocrystals and QDs immobilized in 20% polyacrylamide gel and measured the SHG and fluorescence signal intensities was gradually increased. With increasing illumination power the signal intensity of SHG nanoprobes rises quadratically, following a second order nonlinearity response (as shown in FIG. 1d). In contrast, QDs signal strength saturation occurs at low power levels. In addition, random blinking intervals of QDs become more apparent when increasing the illumination intensity. As the illumination intensity is increased 40-fold, the SHG signal of $BaTiO_3$ nanocrystals gets more than 2 orders of magnitude stronger than the starting value. Increasing the illumination power further resulted in even higher signal intensities, well above optimal photomultiplier gain settings. Thus $BaTiO_3$ nanocrystals don't saturate at high irradiation levels, eventually outperforming any fluorescent dye with increasing power levels. This permits SHG nanoprobes to offer very sensitive and rapid detection of molecules of interest without compromising on temporal resolution by simply increasing the illumination power.

EXAMPLE 2

SHG Nanoprobe Imaging

To test whether SHG nanoprobes can be detected in live vertebrate tissue, BaTiO$_3$ nanoparticles were injected into one-cell stage zebrafish embryos and imaged. More specifically, in this example the SHG nanocrystal probes of the current invention, BaTiO$_3$ nanocrystals were injected into zebrafish embryos. Several days after cytoplasmic injection (around 72 hpf) excitation of nanocrystals with femtosecond pulsed 820 nm light results in strong SHG signal detectable in epi-direction as well as in trans-direction throughout the whole zebrafish body.

The injected embryos developed indistinguishably from their uninjected counterparts, demonstrating that barium titanate is physiologically inert and non-toxic to the sensitive zebrafish embryonic cells. Bright signal could be detected superficially and deep within the tissue. Even in deep tissues and organs, the imaging required only low levels of illumination intensity. The in vivo SHG intensity spectra were identical to that obtained in vitro.

Figure 2A:
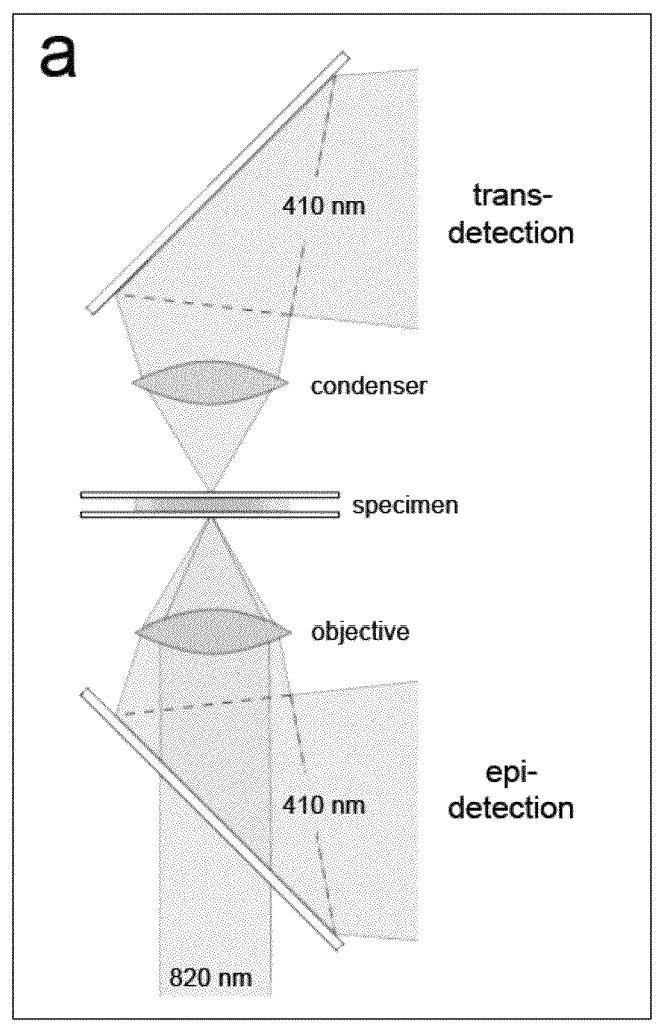

The results of the experiment are shown in the photographic plates provided in FIGS. 2b to 2f, the low energy excitation of the probe nanocrystals results in a strong second harmonic signal. (the bright point of light in the center of the image in FIG. 2a). This signal is detectable in epi-mode (FIG. 2a) as well as in trans-mode (FIG. 2b) throughout the whole zebrafish body (nanocrystal indicated at arrowhead in FIGS. 2a to 2c), proving the coherence of the technique. In contrast, the endogenous second harmonic signal from the tail-muscles can only be detected with relatively high energy excitation in the trans-mode (FIG. 2b). (For discussion, see, e.g., P. J. Cannpagnola, L. M. Loew, *Nat Biotechnol* 21, 1356 (November, 2003); and P. J. Cannpagnola, et al., *J Biomed Opt* 6, 277 (July, 2001), the disclosures of which are incorporated herein by reference.) FIG. 2d provides an image developed from injecting a conventional. Bodipy TR methyl ester dye to label the extracellular matrix and cell membranes. FIG. 2e provides a merged picture showing the signal from the inventive probe combined with the images of the tissue developed from other techniques.

This exemplary image shows that the SHG nanocrystal probes of the current invention provide superb signal-to-noise ratio after in vivo injections allowing detection in rather deep organs, as well as the potential for real-time biodistribution monitoring. In addition, unlike endogenous second harmonic generation from ordered, noncentrosymmetric structures like collagen or myosin, which can only be detected in trans-mode, SHG nanocrystals can be detected both in trans-mode as well as in epi-mode allowing for the ability to isolate the probe signal from the background signal generated by the surrounding biological structures.

EXAMPLE 3

Field Resonance Enhanced Second Harmonic Technique

In addition to simple second harmonic imaging using the second harmonic generating nanoprobes of the current invention, the nanoprobes may also be used in a field resonance enhanced mode to allow access to a number of biological processes that can occur below the nanosecond time frame. Using this field resonance enhanced second harmonic (FRESH) technique in accordance with the current invention it is possible to examine the dynamics of biological processes with high sensitivity and spatiotemporal resolution.

To understand the potential importance of the FRESH technique it is necessary to examine the inner workings of most biological processes. Besides having highly complex three-dimensional. (3D) structures spanning a large range of length scales, living organisms by their nature are very dynamic: molecular processes such as protein, DNA, and RNA conformations—that take place in a timescale ranging from 100 fs to 100 s while the organisms move and metabolize—as well as molecule-molecule interactions such as, but not limited to, protein-protein, protein-DNA, and protein-RNA interactions. (See, e.g., Whitesides, G. M., Nat. Biotechnol. 21, 1161-1165 (2003); Williams, S. et al., Biochemistry 35, 691-697 (1996); Gilmanshin, R., et al., Proc. Natl. Acad. Sci. U.S.A. 94, 3709-3713 (1997); Callender, R. H., et al., Annual. Review of Physical. Chemistry 49, 173-202 (1998); Trifonov, A. et al., Journal of Physical Chemistry B 109, 19490-19495 (2005); Cheatham, T. E., Curr. Opin. Struct. Biol. 14, 360-367 (2004); Millar, D. P., Curr. Opin. Struct. Biol. 6, 322-326 (1996); and Brauns, E. B., et al., Physical Review Letters 88 (2002), the disclosures of which are incorporated herein by reference.) The understanding of these processes not only has fundamental biological significance, but could also enable the treatment of a host of human diseases. For example, it has been shown that a variety of serious diseases can be directly linked to protein misfolding. (See, e.g., Ding, F., et al., J. Biol. Chem. 280, 40235-40240 (2005); and Dobson, C. M., Philos. Trans. R. Soc. Lond. B 356, 133-145 (2001), the disclosures of which are incorporated herein by reference.)

Fluorescence resonance energy transfer (FRET) and its associated techniques have achieved great success in probing molecular activities. (See, e.g., Selvin, P. R. Nat. Struct. Biol. 7, 730-734 (2000); Greulich, K. O., ChemPhysChem 6, 2458-2471 (2005); Peter, M. & Ameer-Beg, S. M. FLIM. Biol. Cell 96, 231-236 (2004); Day, R. N. & Schaufele, F., Mol. Endocrinol. 19, 1675-1686 (2005); Wallrabe, H. & Periasamy, A., Curr. Opin. Biotechnol. 16, 19-27 (2005); Piehler, J., Curr. Opin. Struct. Biol. 15, 4-14 (2005); Chen, Y., et al., Differentiation 71, 528-541 (2003); Truong, K. & Ikura, M. Curr. Opin. Struct. Biol. 11, 573-578 (2001); Zal, T. & Gascoigne, N. R., Curr. Opin. Immunol. 16, 418-427 (2004); and Miyawaki, A., Dev. Cell 4, 295-305 (2003), the disclosures of which are incorporated herein by reference.) However, these techniques still have the same basic limitations of fluorescence discussed above, including blinking, bleaching, and saturation, which restricts the sensitivity, signal-to-noise ratio, and spatiotemporal resolution. The integration of the nanoprobes of the current invention with a field resonance enhancement technique in the FRESH protocol set forth herein allows for greatly improved capabilities for the spatiotemporal visualization/detection of (single) molecule conformation changes or molecule-molecule interactions.

Figure 3:
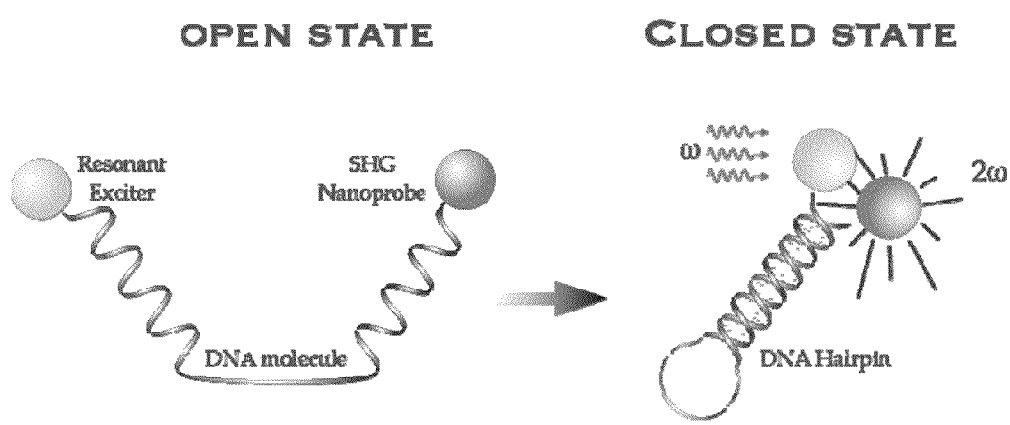
FIG. 3 provides a schematic diagram of the principles of operation of an exemplary embodiment of the FRESH sensing technique using an SHG nanoprobe in accordance with the current invention.

The basic principle of the FRESH technique is illustrated in FIG. 3, where a simple DNA hairpin molecule is used as an example. In the FRESH methodology, two dissimilar types of nanostructures are used to label molecules of interest. First, an exciter nanostructure that resonates at the frequency of the pump is attached to the molecule. Such a structure may be a metal nanostructure, such as, for example, Au-nanorods, Au-nanospheres or Au-nanoshells, and other materials as well. Second, a probe nanostructure that generates a second harmonic signal in accordance with the current invention is attached to the molecule. As before such a probe nanostructure can be any construct organic, inorganic or a combination thereof that does not possess an inversion symmetry.

Figure 4:
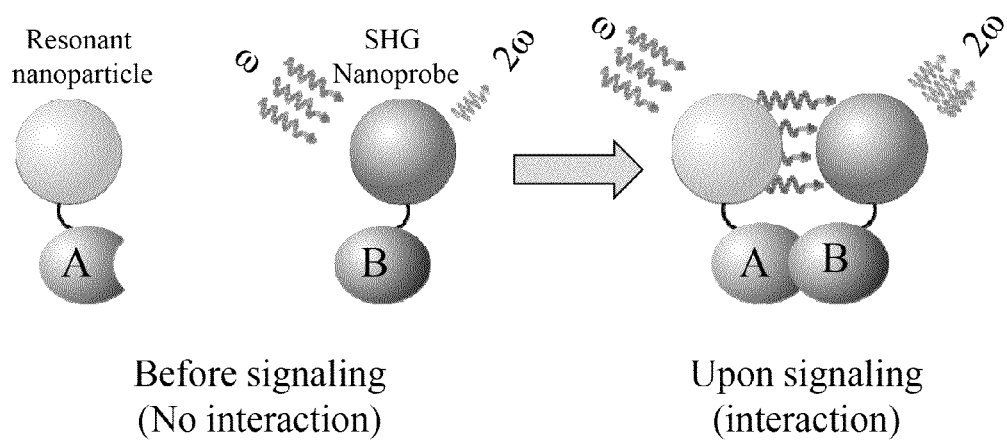
FIG. 4 provides a schematic diagram of the principles of operation of a second exemplary embodiment of the FRESH sensing technique using an SHG nanoprobes in accordance with the current invention.

It should also be understood that although a simple DNA hairpin structure is shown as an example in FIG. 3, the FRESH methodology of the current invention is equally applicable to other biological processes and structures, such as, for example, protein folding or protein-protein interaction. Alternatively, the technique may be used as biosensor to detect any phenomenon of interest. FIG. 4, provides a schematic diagram of the operation of such a sensor, the operation of which will be discussed generically below.

During operation of the SHG probes of the current invention, as shown in FIGS. 3 and 4 above, a continuous wave, modulated or pump energy source, such as a laser emission is focused on a sample of interest. When the exciter nanostructure is energized at the resonance frequency of the energy source, the exciter enhances the electric field within a few nanometers of its vicinity. (See, e.g., Averitt, R. D., Westcott, S. L. & Hales, N. J., J. Opt. Soc. Am. B 16, 1824-1832 (1999), the disclosure of which is incorporated herein by reference.) This enhanced local field couples with neighboring probes when brought within a few nanometers of a probe nanostructure. The coupling of the pump nanostructure with the probe nanostructure enhances the second harmonic emission from the probe nanostructure by orders of magnitude allowing for detection of the second harmonic emission. Similar effects have been demonstrated in Surface Enhanced Raman Spectroscopy (SERS) with an enhancement factor of $10^{14}$. (See, e.g., Nie, S. M. & Emery, S. R., Science 275, 1102-1106 (1997), the disclosure of which is incorporated herein by reference.) The enhanced electric field around the resonant exciter can serve as a ruler of nanometer resolution enabling high resolution imaging. The FRESH technique also allows for the (in vivo/in vitro) imaging of biological processes such as cell signaling, neuroimaging, protein conformation probing, DNA conformation probing, gene transcription, and virus infection and replication in cells in real time.

EXAMPLE 4

Direct Nucleic Acid Sequencing Using SHG Nanoprobes

The sequence of DNA constitutes the heritable genetic information in nuclei, plasmids, mitochondria, and chloroplasts forming the basis for the developmental programs of all living organisms. Determining the sequence of nucleic acid samples is therefore essential in basic research studying fundamental biological processes, as well as in applied fields such as diagnostic or forensic research.

Rapid sequencing attained with modern DNA sequencing technology has significantly accelerated biological research, like the large-scale sequencing of the human genome in the Human Genome Project. (See, e.g., E. S. Lander et al., Nature 409, 860 (Feb. 15, 2001); and J. C. Venter et al., Science 291, 1304 (Feb. 16, 2001), the disclosures of which are incorporated herein by reference.) Further improvements will significantly impact personalized medicine, tailoring medical care to an individual's needs by gene expression profiling. Hence, understanding our genomes may help delay or even prevent disease. For patients suffering from genetic illnesses, personal genetic information may determine which medicines will drive their disease into remission without negative side effects. (See, H. Bosnjak, K. Pavelic, S. K. Pavelic, EMBO Rep 9, 1056 (November, 2008), the disclosure of which is incorporated herein by reference.)

In the human genome, about 3 billion bases are arranged along the chromosomes in a particular order for each unique individual. The high demand for low cost, ultrasensitive, and ultrafast sequencing has given rise to a number of high-throughput sequencing technologies. (See, e.g., Shendure, R. D. Mitra, C. Varma, G. M. Church, Nat Rev Genet 5, 335 (May, 2004); N. Hall, J Exp Biol 210, 1518 (May, 2007); and J. A. Shendure, G. J. Porreca, G. M. Church, Curr Protoc Mol Biol, Chapter 7, Unit 7 1 (January, 2008), the disclosures of which are incorporated herein by reference.) All of these approaches have two aspects in common: 1) parallelization of the sequencing process to produce millions of sequences at once, and 2) detection methods based on fluorescent labels.

However as previously discussed, detection methods based on optical imaging utilizing photons as information source present numerous disadvantages that have a significant impact on the signal strength, including: 1) dye saturation, because the number of photons emitted by the fluorophore in a given time is restricted by the excited state lifetime, 2) dye bleaching, which limits the total number of photons per dye, and 3) dye blinking, the intrinsic fluorescence intermittency of single fluorescent labels which does not allow fast and continuous detection of individual molecules, complicating considerably the data analysis.

To improve the sensitivity of the molecular detection methods, most techniques use an in vitro cloning step amplifying individual. DNA molecules. (See, e.g., M. Margulies et al., Nature 437, 376 (Sep. 15, 2005); J. Shendure et al., Science 309, 1728 (Sep. 9, 2005); and L. W. Hillier et al., Nat Methods 5, 183 (February, 2008), the disclosures of which are incorporated herein by reference.) Although those methods have been used successfully to sequence microbial genomes, in particular the use of polymerase chain reaction (PCR) amplification may limit broad application to human genome sequencing. The use of PCR is problematic for several reasons: 1) PCR introduces an uncontrolled bias in template representation as amplification efficiencies vary as a function of template properties, and 2) errors can be introduced since the fidelity of PCR polymerases is widely reported at $0.5\text{-}1.0\times 10^{-4}$, which is a considerable error rate for amplification of single-molecule targets. (See, e.g., W. M. Barnes, Gene 112, 29 (Mar. 1, 1992), the disclosure of which is incorporated herein by reference.)

Skipping the amplification step by performing a single-molecule sequencing approach would help to ameliorate these limitations. (See, e.g., I. Braslaysky, B. Hebert, E. Kartalov, S. R. Quake, Proc Natl Acad Sci USA 100, 3960 (Apr. 1, 2003); and T. D. Harris et al., Science 320, 106 (Apr. 4, 2008), the disclosures of which are incorporated herein by reference.) However, such methods still distinguish low abundance targets using common fluorescent probes with their obvious disadvantages—dye saturation, bleaching, and blinking—that will ultimately result in poor signal-to-noise ratio (SNR) in a very short detection time frame. To improve the signal long integration times must be used, sacrificing rapidity of data acquisition and thereby limiting also its broad application to ultrafast human genome sequencing.

The current invention overcomes these limitations by employing a distinct set of SHG nanoprobes in a new Multi-SHG Detection Imaging (MSDI) modality, which provides specificity, superb sensitivity and outstanding rapidity for DNA sequencing. In particular, by tuning the excitation wavelength from 780 to 970 nm in a conventional two-photon microscope SHG signal from $BaTiO_3$ nanocrystals can be detected with intensity peaks ranging from 380 up to 485 nm. The highest efficiency is achieved when the excitation wavelength is tuned to lower wavelengths. Exploiting these signal profile characteristics, a multi-SHG imaging modality can be set up where one can discriminate between two different types of nanocrystals by detecting SHG signal intensities at two distinct excitation wavelengths (e.g. 800 nm versus 880 nm). This is highly relevant in multi-label co-localization imaging, allowing detection of distinct SHG nanomaterials in parallel.

It should be understood that other wavelengths can also be used dependent on the materials serving as SHG nanoprobes attached to the four nucleotide bases A, C, G, or T (U) each. In addition, these emissions can be detected by any optical based technique, such as, for example, continuous wave, modulated, or other pulsed lasers having for example nano, pico, femto, or attosecond timeframes.

Unlike currently used fluorescent probes attached to nucleotides for DNA sequencing, SHG nanoprobes neither bleach nor blink, and the signal does not saturate with increasing illumination intensity. And whereas fluorescence involves real energy transition of electrons, SHG involves only virtual energy transition. As a result, using ultrafast (e.g. attosecond or femtosecond) pulsed lasers the response time of SHG is at the attosecond or femtosecond level, about several orders of magnitude faster than the nanosecond response time of fluorescence. This permits SHG nanoprobes to offer very sensitive and rapid DNA sequencing detection of indefinite length, with ultrafast acquisition rates combined with superb SNR.

This MSDI application of the SHG nanoprobes is based on linking each nucleotide with a distinct SHG nanoprobe to provide unique signal profile characteristics for each nucleotide. In this embodiment, distinct nanocrystals of the size of ≤100 nm that do not possess an inversion symmetry and therefore generate second harmonic signals which can be detected by conventional two-photon microscopy would be linked to different nucleotides of interest to provide individualized fingerprints for each nucleotide.

To demonstrate how such an MSDI process would work emission data was obtained for three different nanoprobe materials at different wavelengths.

Figure 5A:
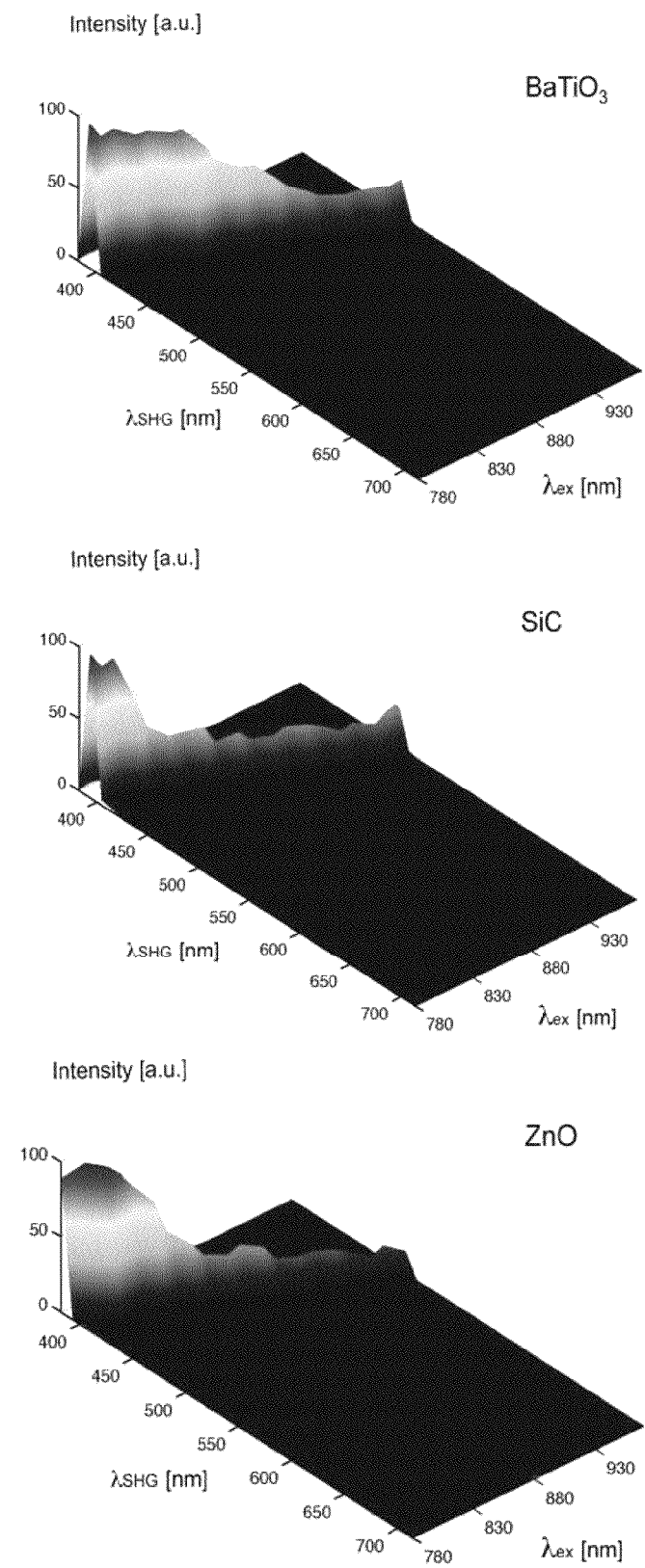
FIG. 5a displays the 3D normalized second harmonic emission data of $BaTiO_3$/SiC/$KNbO_3$ nanocrystals (emission ranging from 380 to 710 nm) generated by conventional two-photon excitation (excitation ranging from 760 to 970 nm)

FIG. 5a displays the 3D normalized second harmonic emission data of the $BaTiO_3$, SiC, and $KNbO_3$ nanocrystals (emission ranging from 380 to 710 nm) generated by conventional two-photon excitation (excitation ranging from 760 to 970 nm). These graphs show that each of the $BaTiO_3$/SiC/$KNbO_3$ nanocrystals display distinct SHG signal profiles; $BaTiO_3$ is still detectable at longer illumination wavelengths. Exploiting these signal profile characteristics, an MSDI modality can be developed where it is possible to discriminate between several types of nanocrystals by detecting SHG signal intensities with (at least two) distinct excitation wavelengths.

Figure 5B:
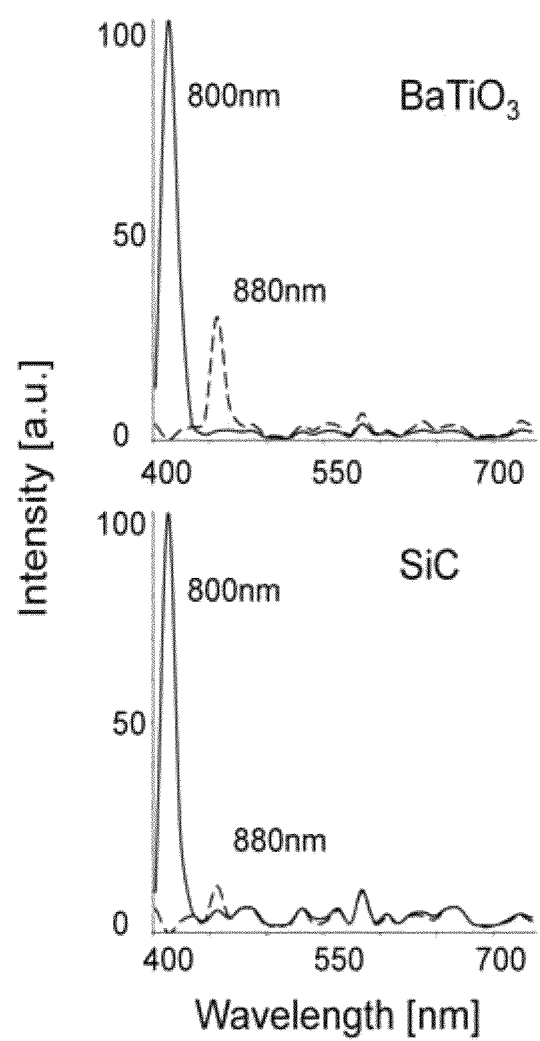
FIG. 5b displays normalized SHG signal spectra of $BaTiO_3$ (upper) and SiC (lower) nanocrystals generated by tuning the excitation wavelength to 800 nm (solid line) and 880 nm (dashed line)
Figure 5C:
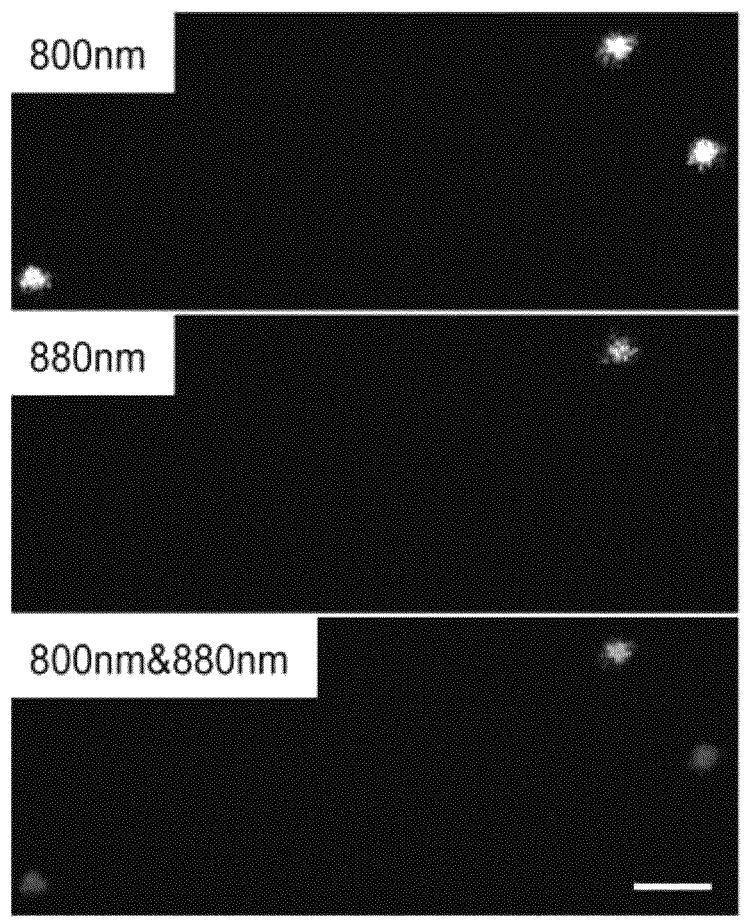
FIG. 5c shows the principle of the Multi-SHG Detection Imaging (MSDI) modality where one can discriminate between two different types of SHG nanoprobes (immobilized $BaTiO_3$ and SiC nanocrystals) by detecting SHG signal intensities at two distinct excitation wavelengths (e.g. 800 nm versus 880 nm).

FIG. 5b displays normalized SHG signal spectra of $BaTiO_3$ (upper) and SiC (lower) nanocrystals generated by tuning the excitation wavelength to 800 nm (solid line) and 880 nm (dashed line). In comparison, FIG. 5c shows single confocal sections showing comparable SHG signal intensities of immobilized $BaTiO_3$ and SiC nanocrystals in parallel. The non-centrosymmetric nanomaterials were sequentially excited with 800 nm (upper) and 880 nm (middle), respectively. Whereas the SHG signal of SiC nanocrystals is only readily detectable at 800 nm, the SHG signal of $BaTiO_3$ nanocrystal is visible at both excitation wavelengths. In a multi-SHG imaging modality these relative intensities are sufficient to be compared in order to distinguish different SHG nanoprobe materials. Applying this information it is possible to distinguish both nanomaterials.

Figure 6:
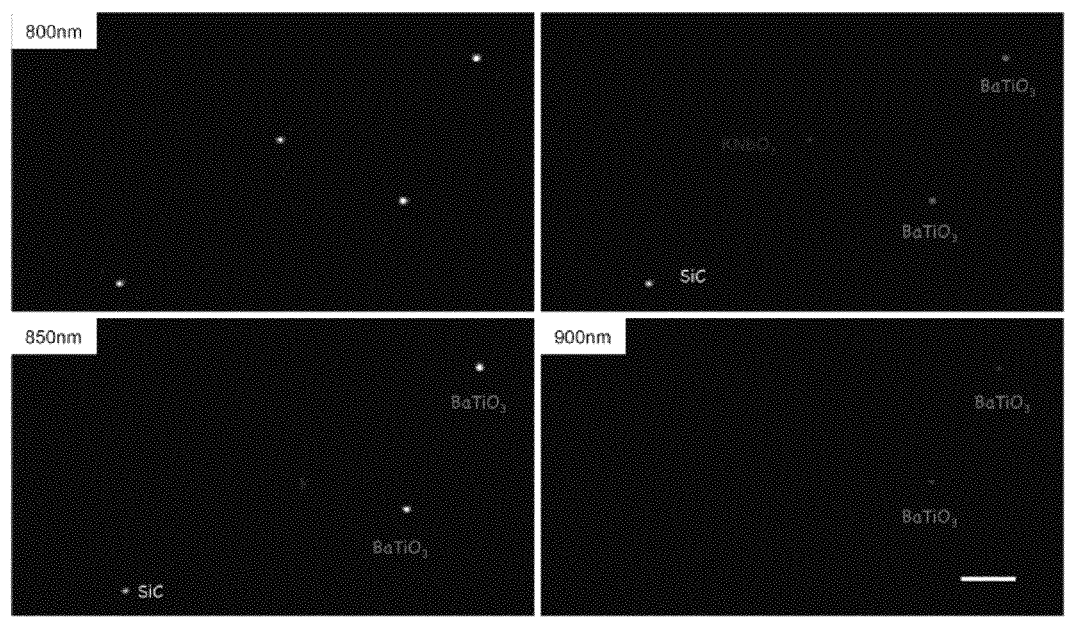
FIG. 6 provides another Multi-SHG Detection Imaging (MSDI) modality demonstration with SHG signal profiles of $BaTiO_3$/SiC/$KNbO_3$ using excitations at 800 nm/850 nm/900 nm and emission detections at 400 nm/425 nm/450 nm.

FIG. 6 provides a second example of using the Multi-SHG Detection Imaging (MSDI) Modality to exploit the distinct SHG signal profiles of three materials ($BaTiO_3$/SiC/$KNbO_3$) using excitations at 800 nm/850 nm/900 nm and emission detections at 400 nm/425 nm/450 nm. Single confocal sections showing comparable SHG signal intensities of immobilized $BaTiO_3$ nanocrystals, SiC nanocrystals, and KNbO3 nanorods in parallel are provided. In this example, the non-centrosymmetric nanomaterials were sequentially excited with 800 nm (upper left), 850 nm (lower left), and 900 nm (lower right), respectively wavelength light. Whereas the SHG signal of KNbO3 nanorods is detectable only at 800 nm, the SHG signal of SiC nanocrystals is visible at 800 nm and 850 nm excitation wavelengths. However only $BaTiO_3$ nanocrystals are detectable at all three wavelength settings. Using these different emissive characteristics it is possible to operate the SHG nanocrystals in such a MSDI mode to distinguish the 3 nanomaterials.

Figure 7:
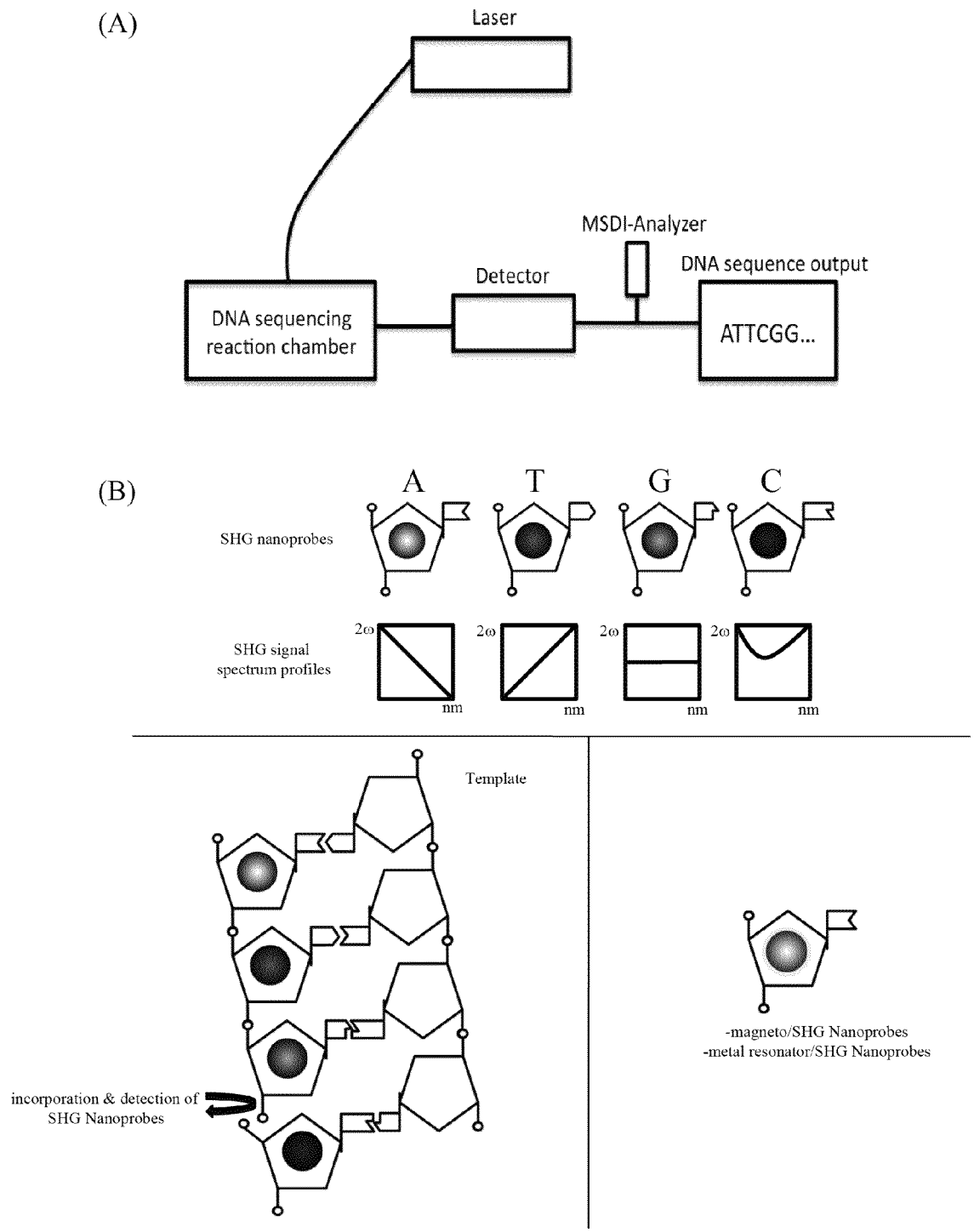
FIG. 7a provides a schematic diagram of the exemplary method of using SHG nanoprobes in a MSDI modality for ultrafast, ultrasensitive, and rapid DNA sequencing.
FIG. 7b provides a schematic scheme of sequencing the four nucleotides linked to distinct SHG nanoprobe during ultrafast, ultrasensitive, and rapid DNA sequencing making using of the MSDI modality, and possible extensions based on the principle of FRESH and VS-SHG.

An exemplary schematic of a setup for integrating the technique of the current invention into conventional sequence technology strategies is shown in FIGS. 7a and 7b. The example demonstrates further that fast MSDI of distinct SHG nanoprobes linked to each of the four nucleotides would allow for the detection of distinct nucleotides during DNA sequencing with high specificity, superb sensitivity and outstanding rapidity, ultimately realizing ultrafast human genome sequencing.

As shown, the present invention provides a novel sequencing method, which offers a cost effective, high throughput method by which nucleic acid molecules from any source can be readily sequenced without the need of prior parallelization/amplification. Using the MSDI modality with four distinct SHG nanoprobes attached to the four nucleotide bases A, C, G, or T (U) each, a rapid sequencing apparatus can be generated which includes, but is not limited to:

First, any macromolecule which catalyzes formation of a polynucleotide sequence can be used as the polymerase. In one embodiment, sequencing is performed with a DNA-dependent DNA polymerase. DNA-dependent DNA polymerases catalyze the polymerization of deoxynucleotides to form the complementary strand of a primed DNA template. Examples of DNA-dependent DNA polymerases include, but are not limited to, the *E. coli* DNA polymerase III holoenzyme, the *E. coli* DNA polymerase I Klenow fragment, the DNA polymerase from *Bacillus stearothermophilus* (Bst), the bacteriophage T4 and T7 DNA polymerases, and polymerases from *Pyrococcus furiosis* (Pfu), and *Thermococcus litoralis* (Vent), *Thermus aquaticus* (Taq). Alternatively, where RNA is used as template, a reverse transcriptase—an RNA-dependent DNA polymerase—may be employed. This permits the sequencing of RNAs taken directly from tissues, without prior reverse transcription. Examples of reverse transcriptases include, but are not limited to, reverse transcriptase from Human Immunodeficiency Virus-1 (HIV-1), Avian Myeloblastosis Virus (AMV), and Moloney Murine Leukemia Virus. As an extension, when RNA copies are desired of the sample or target DNA strand being sequenced, RNA polymerases can be used. Examples of these enzymes include, but are not limited to, from RNA polymerases from the bacteriophages T7, T3, SP6 as well as from *E. coli*. RNA-dependent RNA polymerases can also be employed when a RNA copy of a sample RNA is desired/sequenced. RNA-dependent RNA polymerases from bromoviruses, tobamoviruses, tombusvirus, leviviruses, hepatitis C-like viruses, and picornaviruses among others can be used.

Second, the nucleic acid to be sequenced can be obtained from any source. Example nucleic acid samples to be sequenced include double-stranded DNA, single-stranded DNA, DNA from plasmid, first strand cDNA, total genomic DNA, RNA, cut/end-modified DNA (e.g. with RNA polymerase promoter), in vitro transposon tagged (e.g., random insertion of RNA polymerase promoter).

Third, various primers and promoters are known in the art and may be suitable for sequence extension using the MSDI modality. Examples include random primers, anchor point primer libraries, single-stranded binding protein masking/primer library, and primase.

Fourth, four distinct SHG nanoprobes attached to the four nucleotide bases A, C, G, or T (U) each will be used. Such a structure may be any organic, inorganic or combination of organic and inorganic nanocrystal, such as, for example $BaTiO_3$, SiC, ZnO, ZnS, ZnSe, ZnTe, CdS, CdSe, CdTe, GaAs, GaSb, GaP, GaN, InSb, $LiNbO_3$, $KNbO_3$, $KTiOPO_4$, $Fe(IO_3)_3$, Au, Ag, N-(4-nitrophenyl)-(L)-prolinol (NPP), urea, 4-Nitroaniline, 2-Methyl-4-nitroaniline (MNA), 3-Methyl-4-methoxy-4'-nitrostilbene), β-$BaB2O4$ (Beta-Barium Borate/BBO, $LiB3O5$ (Lithium Triborate/LBO), $LiNbO3$ (Lithium Niobate/LN), $KTiOPO4$ (Potassium Titanyl Phosphate/KTP), $AgGaS2$ (Silver Thiogallate/AGS), $AgGaSe2$ (Silver Gallium Selenide/AGSe), $ZnGeP2$ (Zinc Germanium Phosphide/ZGP), GaSe (Gallium Selenide), $KH2PO4$ (Potassium Dihydrogen Phosphate/KDP), $NH4H2PO4$ (Ammonium Dihydrogen Phosphate (ADP), $KD2PO4$ (Deuterated Potassium Dihydrogen Phosphate/DKDP), $CsLiB6O10$ (Cesium Lithium Borate/CLBO), $KTiOAsO4$ (Potassium Titanyl Arsenate/KTA), $KNbO3$ (Potassium Niobate/KN), $LiTaO3$ (Lithium Tantalate/LT), $RbTiOAsO4$ (Rubidium Titanyl Arsenate/RTA), $BaTiO_3$ (Barium Titanate), $MgBaF4$ (Magnesium Barium Fluoride), GaAs (Gallium Arsenide), $BiB3O6$ (Bismuth Triborate/BIBO), $K2Al2B2O7$ (Potassium Aluminum Borate/KABO), $KBe2BO3F2$ (Potassium Fluoroboratoberyllate/KBBF), $BaAlBO3F2$ (Barium Aluminum Fluoroborate/BABF), $La2CaB10O19$ (Lanthanum Calcium Borate/LCB), $GdCa4O(BO3)3$ (Gadolinium Calcium Oxyborate/GdCOB), $YCa4O(BO3)3$ (Yttrium Calcium Oxyborate/YCOB), $Li2B4O7$ (Lithium Tetraborate/LB4), $LiRbB4O7$ (Lithium Rubidium Tetraborate/LRB4), $CdHg(SCN)4$ (Cadmium Mercury Thiocyanate/CMTC), $RbTiOPO4$ (Rubidium Titanyl Phosphate/RTP), $LiInS2$ (Lithium Thioindate/LIS), $LiInSe2$ (Lithium Indium Selenide/LISe), $KB5O8.4H2O$ (Potassium Pentaborate Tetrahydrate/KB5), $CsB3O5$ (Cesium Triborate/CBO), $C4H7D12N4PO7$ (Deuterated L-Arginine Phosphate Monohydrate/DLAP), a-$HIO3$ (a-Iodic Acid), $LiCOOH.H2O$ (Lithium Formate Monohydrate/LFM), $CsH2AsO4$ (Cesium Dihydrogen Arsenate/CDA), $CsD2AsO4$ (Deuterated Cesium Dihydrogen Arsenate/DCDA), $RbH2PO4$ (Rubidium Dihydrogen Phosphate/RDP), $CsTiOAsO4$ (Cesium Titanyl Arsenate/CTA), $Ba2NaNb5O15$ (Barium Sodium Niobate/BNN), $K3Li2Nb5O15$ (Potassium Lithium Niobate/KLN), $CO(NH2)2$ (Urea), $LiIO3$ (Lithium Iodate), $Ag3AsS3$ (Proustite), $HgGa2S4$ (Mercury Thiogallate), $CdGeAs2$ (Cadmium Germanium Arsenide/CGA), $Ti3AsSe3$ (Thallium Arsenic Selenide/TAS), CdSe (Cadmium Selenide), ZnO (Zinc Oxide), ZnS (Zinc Sulfide), ZnSe (Zinc Selenide), ZnTe (Zinc Telluride), CdS (Cadmium Sulfide), SiC (Silicon Carbide), and GaN (Gallium Nitride), GaSb (Gallium Antimonide), among others. In addition, the SHG nanoprobes may include magneto-SHG particles, such as, for example, ferromagnetic, ferrimagnetic, paramagnetic, diamagnetic, superparamagnetic (i.e. $Fe3O4$), superdiamagnetic, and metamagentic superparamagnetic material as well as resonant material nanoshells around the SHG nanoprobe particles such as, for example, gold, silver, copper, aluminum, palladium, or platinum.

Fifth, functionalization of SHG nanoprobes may be provided by introducing functional groups on the surface of SHG nanoprobes, including, but are not limited to: sulfhydryl residues, carboxylate groups, primary amine groups, aldehyde residues, and hydrazide functional groups. The targeting to the four nucleotide bases A, C, G, or T (U) may be made by cross-linking reagents, including, but not limited to: zero-length cross-linkers (among them Carbodiimides), homobifunctional cross-linkers (among them NHS esters, imidoesters), heterobifunctional cross-linkers (among them amine-reactive and sulfhydryl-reactive cross-linkers), and trifunctional cross-linkers (among them sulfo-SBED).

Sixth, detection of emission of nucleotides to be sequenced can be detected by any optical based technique, such as, for example, continuous wave, modulated, or other pulsed lasers having for example nano, pico, femto, or attosecond timeframes. The MSDI modality can be set up where one can discriminate between four different types of nanocrystals by detecting SHG signal intensities at least two distinct excitation wavelengths (e.g. 800 nm versus 880 nm).

Seventh, FRESH can be alternatively employed to increase signal to noise ratios. When the exciter nanostructure is energized at the resonance frequency of the energy source, the exciter enhances the electric field within a few nanometers of its vicinity. (See, e.g., Averitt, R. D., Westcott, S. L. & Hales, N. J., J. Opt. Soc. Am. B 16, 1824-1832 (1999), the disclosure of which is incorporated herein by reference.) This enhanced local field couples with neighboring probes when brought within a few nanometers of a probe nanostructure. The coupling of the pump nanostructure with the probe nanostructure enhances the second harmonic emission from the probe nanostructure by orders of magnitude allowing for detection of the second harmonic emission. Similar effects have been demonstrated in Surface Enhanced Raman Spectroscopy (SERS) with an enhancement factor of $10^{14}$. (See, e.g., Nie, S. M. & Emery, S. R., Science 275, 1102-1106 (1997), the disclosure of which is incorporated herein by reference.) In one embodiment, polymerase molecules are tagged with the exciter nanostructure. This would limit their excitation to the active site of the polymerase or any other appropriate part of the polymerase. Such an arrangement would significantly increase the signal-to-noise ratio of nucleotide detection. Such a structure may be a metal nanostructure, such as, for example, Au-nanorods, Au-nanospheres or Au-nanoshells, and other materials as well. In another embodiment, the surface, where detection of emission of nucleotides is performed may be of an exciter material which increases the signal to noise ratio while approaching the SHG-labeled nucleotides to be sequenced. Such a structure may be a metal coating such as, for example, Au or Ag, and other materials as well.

The applications of the method of the present invention includes, but is not limited to:

clinical applications, to diagnose genetic disorders, traits or other features predictable from primary DNA sequence information, such as prenatal, neo-natal and post-natal diagnoses or detection of congenital disorders or to analyze somatic disease caused by genetic recombination and/or mutation, identify loss of heterozygosity, point mutations, or other genetic changes associated with cancer, or present in pre-cancerous states. Alternatively, the methods of the present invention can also be used to identify disease-causing pathogens (e.g., viral, bacterial, fungal) by direct sequencing of affected tissues.

agricultural applications, to identify plant and animal pathogens, and designing methods of combating them or to reveal genetic variation underlying both desirable and undesirable traits in agriculturally important plants and animals.

tumor diagnosis to generate a genetic profile from individual tumors, allowing researchers to follow precisely what genetic changes accompany various stages of tumor progression. This information will also permit the design of specific agents to target cancer cells for tailor-made assaults on individual tumors.

criminal and forensic investigations to determinate paternity/maternity by genetically identifying samples of blood, hair, skin and other tissues to unambiguously establish a link between a suspected individual and forensically relevant samples.

research to sequence whole genomes or large genomic segments of transformed cells to select individuals with the desired integration status.

as will be discussed in greater detail below, a special class of VS-SHG nanoprobes may also be used for sequencing applications, allowing for the measurement of electric fields during and after sequencing.

EXAMPLE 5

Optical Monitoring of Electric Fields Using VS-SHG Nanoprobes

In another exemplary embodiment, the SHG nanoprobes of the current invention may also be used to monitor electric fields in vivo or in silico.

Proper functioning of biological processes like motor coordination, sensory processing or cardiac rhythm depends critically on the presence of electric fields. Electric fields are located in cells, associated with the mitochondrial membrane, and surround living cells, across cellular membranes of neuronal cells. Changes in electric fields can indicate perturbations, such as the reduction of the electric field associated with the neuronal membrane potential in Alzheimer's disease, as well as cell death, the loss of the electric field associated with the mitochondrial membrane. (See, e.g., B. J. Blanchard, V. L. Thomas, V. M. Ingram, *Biochem Biophys Res Commun* 293, 1197 (May 17, 2002); and J. S. Kim, L. He, J. J. Lemasters, *Biochem Biophys Res Commun* 304, 463 (May 9, 2003), the disclosures of which are incorporated herein by reference.) In addition, externally applied electric fields have profound effects on cellular processes, such as wound healing, growth, and regeneration. (See, e.g., R. Nuccitelli, *Curr Top Dev Biol* 58, 1 (2003); M. Zhao et al., *Nature* 442, 457 (Jul. 27, 2006); and C. D. McCaig, A. M. Rajnicek, B. Song, M. Zhao, *Physiol Rev* 85, 943 (July, 2005), the disclosures of which are incorporated herein by reference.) Recently, electric field irradiation has been also successfully applied in anti-tumor therapies. (See, E. D. Kirson et al., *Proc Natl Aced Sci USA* 104, 10152 (Jun. 12, 2007), the disclosure of which is incorporated herein by reference.) Both external and internal cellular electric fields have strong wide-ranging biological effects and measuring electric fields of cells will greatly enhance our understanding of biological processes.

Optical imaging has been shown to be an ideal technique to track changes in electric fields associated with e.g. the activity of individual neurons, part of a neuron or neuronal populations. Several optical properties of membrane-bound dyes, such as hemi-/mero-cyanine, oxonol or styryl dyes, are sensitive to membrane potential changes, using mechanisms spanning fluorescence, absorption, dichroism to birefringence. (See, B. J. Baker et al., *Cell Mol Neurobiol* 25, 245 (March, 2005), the disclosure of which is incorporated herein by reference.) Likewise, another group of organic dyes or genetically encoded fluorophores employing fluorescence energy transfer (FRET) are sensitive to ion concentrations. (See, e.g., R. Y. Tsien, *Annu Rev Neurosci* 12, 227 (1989); and A. Miyawaki, *Neuron* 48, 189 (Oct. 20, 2005), the disclosures of which are incorporated herein by reference.)

Whereas the first class of optical dyes provide a direct, fast, and linear measure of the change electric fields of stained membranes, optical probes sensing ion concentrations are rather slow to respond due to a slow redistribution of permeant ions from the extracellular medium into the cell. Moreover, they may act as buffers of the ions to be analyzed. This eventually can cause a condition where the ion signal in the presence of the optical probe may substantially outlast the change that would occur in the absence of the probe. In addition, as discussed previously, all conventional classes of fluorescent probes show further limitations: 1) dye saturation, because the number of photons emitted by the fluorophore in a given time is restricted by the excited state lifetime, and 2) dye bleaching, which limits the total number of photons per dye. In addition, autofluorescence from tissue organic components due to illumination absorption can severely limit the signal-to-noise ratio. (See, N. Billinton, A. W. Knight, *Anal Biochem* 291, 175 (Apr. 15, 2001), the disclosure of which is incorporated herein by reference.) Ultimately these dyes reach fractional signal changes (dl/l) of only ~30% at best upon physiological membrane potential changes of 100 mV. (See, B. J. Baker et al., cited above.)

The current invention addresses the above drawbacks with a new class of voltage-sensitive second harmonic generating (VS-SHG) nanoprobes that are suitable for the study of electric fields. This invention is based on using nonlinear materials sensitive to electric field changes: various kinds of nanocrystals of the size of ≤10 μm that do not possess an inversion symmetry and therefore generate voltage-sensitive second harmonic signals (emission ranging from e.g. 350 to 600 nm), which can be detected by conventional two-photon microscopy (tuning the wavelength from 700 to 1200 nm), although other wavelengths might be used dependent on the material to be imaged. It is understood that these emissions can be detected by any optical based technique, such as, for example, continuous wave, modulated, or other puked lasers having for example nano, pico, femto, or attosecond timeframes (See, e.g., R. W. Boyd, *Nonlinear optics* (Academic Press, San Diego, Calif., ed. 2nd, 2003), pp. xvii, 578 p; and W. Denk, J. H. Strickler, W. W. Webb, *Science* 248, 73 (Apr. 6, 1990), the disclosures of each of which are incorporated herein by reference.)

Figure 8:
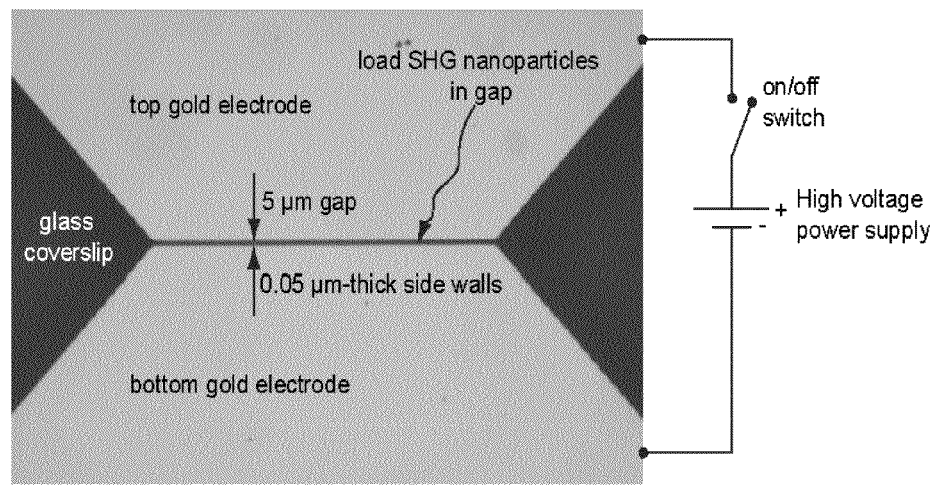
FIG. 8 provides a diagram of an experimental setup for the application of electric fields on exemplary VS-SHG nanoprobes.

In the current example, electric fields were generated by connecting a commercial high voltage power supply to a microfabricated pair of electrodes. To produce the electrodes, a 0.05 μm thick layer of gold was lithographically patterned onto a glass coverslip, as shown in FIG. 8. The gap between the top and bottom electrodes was defined to be 5 μm. Next each electrode was electrically connected to the plus and minus terminals of the high voltage power supply. A manual switch was used to turn the voltage on or off. The coverslip was then mounted on a commercial two-photon microscope.

A small amount (5-7 µl) of VS-SHG nanoprobes, which were dispensed in ethanol, was carefully pipetted onto the area containing the gap.

The electric field, E, within the gap between two long parallel plates may be approximated as:

$$E = V/d \quad \text{(Eq. 2)}$$

where V is the applied voltage and d is the gap size. Given the known spacing of the electrodes, it is therefore trivial to calculate the electric field at any applied voltage. As a non-limiting example, a voltage of 300 V would correspond to a field of 600 kilovolts per centimeter (kV/cm). The physiological range of electric field across a cell membrane is approximately 200 kV/cm.

Figure 9A:
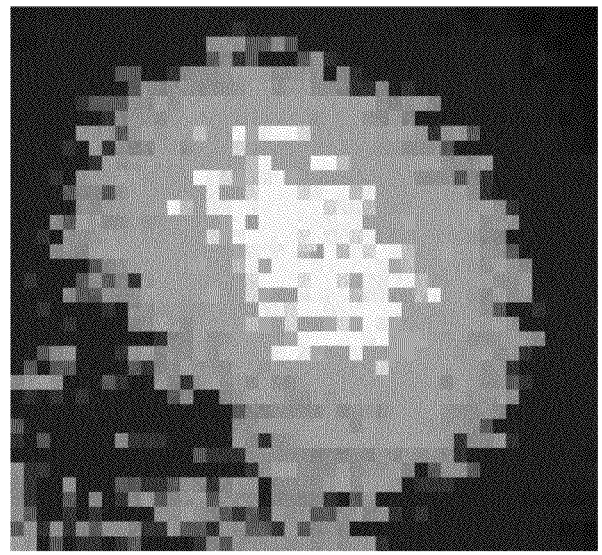
FIGS. 9a to 9c provides data plots for the operation of exemplary VS-SHG nanoprobes in accordance with the current invention.
Figure 9B:
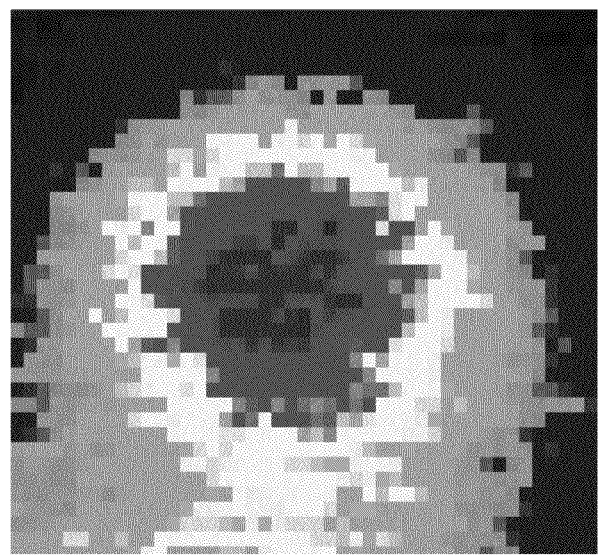
Figure 9C:
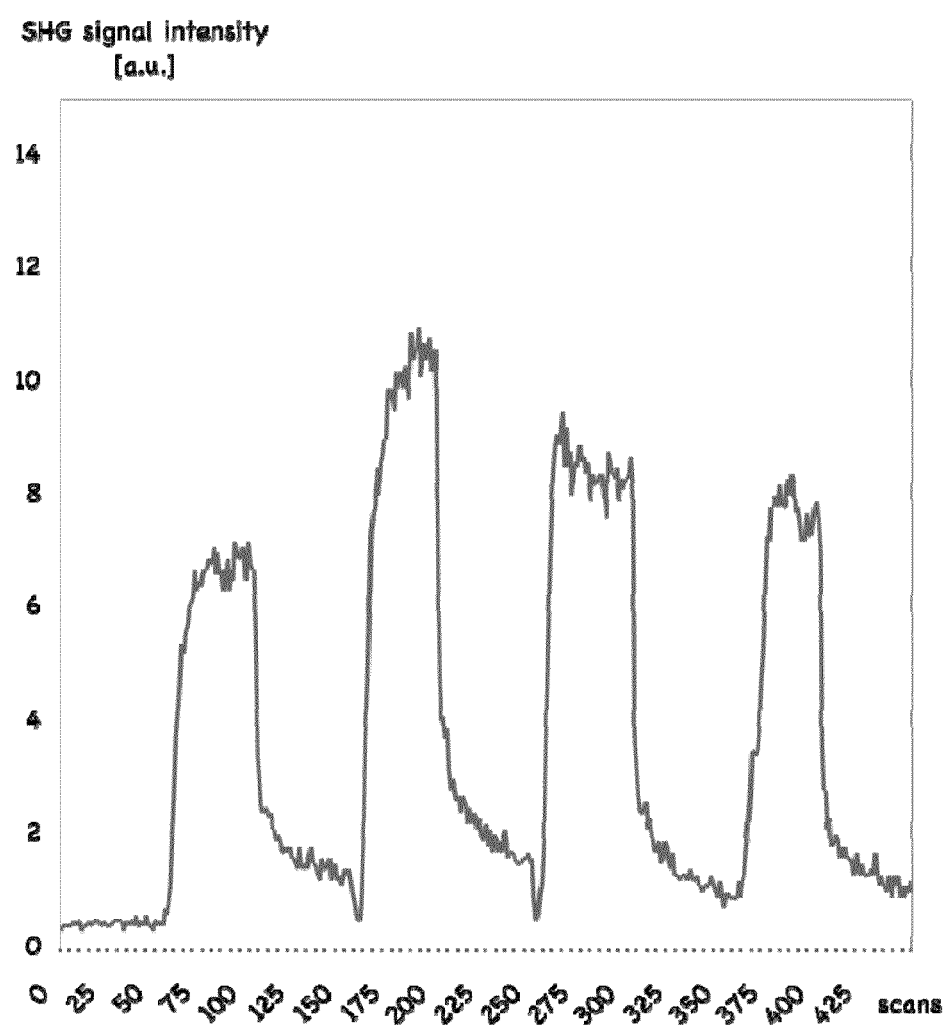

In an exemplary embodiment, the results of which are summarized in FIGS. 9a to c, VS-SHG nanocrystal signal emissions were stimulated by external electric fields. In this example, $BaTiO_3$-nanocrystal emission are generated by conventional two-photon excitation at 800 nm without (9a), and with (9b) an electric field stimulus of 600 kV/cm, which corresponds to roughly 3 times the physiological membrane potential rang. During 450 scans alternating external electric field pulses of 300 were applied for approximately 50 scans and the SHG signal of $BaTiO_3$-nanocrystals was recorded. In this case, the voltage-sensitive second harmonic signal at 400 nm of VS-SHG nanoprobes was recorded by conventional two-photon microscopy (wavelength tuned to 800 nm) during which alternating external electric field pulses were applied at a scan speed of approximately 8 frames per second. As shown, under these experimental conditions VS-SHG nanoprobes—unlike commonly used voltage-sensitive probes—can reach signal changes of up to 10-fold upon electric field stimuli of 600 kV/cm combined with a fast on- and off-rate.

These results demonstrate that VS-SHG nanoprobes have the signal sensitivity for a number of applications, including, for example, in vivo/in vitro quantitative and qualitative evaluation of biological processes like neuronal activity, wound healing, growth, and regeneration as well as tumor imaging and cancer therapy evaluation.

One exemplary method for applying VS-SHG nanoprobes in biological evaluations involves the following procedure.

First, the surface of the VS-SHG nanoparticles would be modified to prevent particle aggregation and facilitate incorporation into the ~5 nm thick hydrophobic cell membrane. As discussed previously, the surface coating would likely consist of two ends; one would adhere to the surface of the VS-SHG nanoparticle, and the other end would be a hydrophobic chain mimicking the internal structure of a lipid bilayer. At the molecular scale, the surface coating would cover the entire available surface of the VS-SHG nanoparticle and protrude in a roughly perpendicular manner from the surface (as will be fully discussed with regard to FIG. 13, below). The coating could in some instances also consist of an optional third segment that would cause only specific cell receptors to recognize and allow the nanoparticle to "dock" onto the cell membrane surface.

Second, VS-SHG nanoparticles would then be suspended in a solution and delivered into the biological tissue, e.g., a culture of neurons or heart cells, but not limited to these examples. Electrostatic interactions would cause the nanoparticles to be incorporated either directly into the lipid bilayer of the cell membrane, or just on the surface of the lipid bilayer. The lipid bilayer is the region containing the largest voltage gradient in the cell, and is therefore believed to be the most favorable location for voltage sensing applications.

Figure 10:
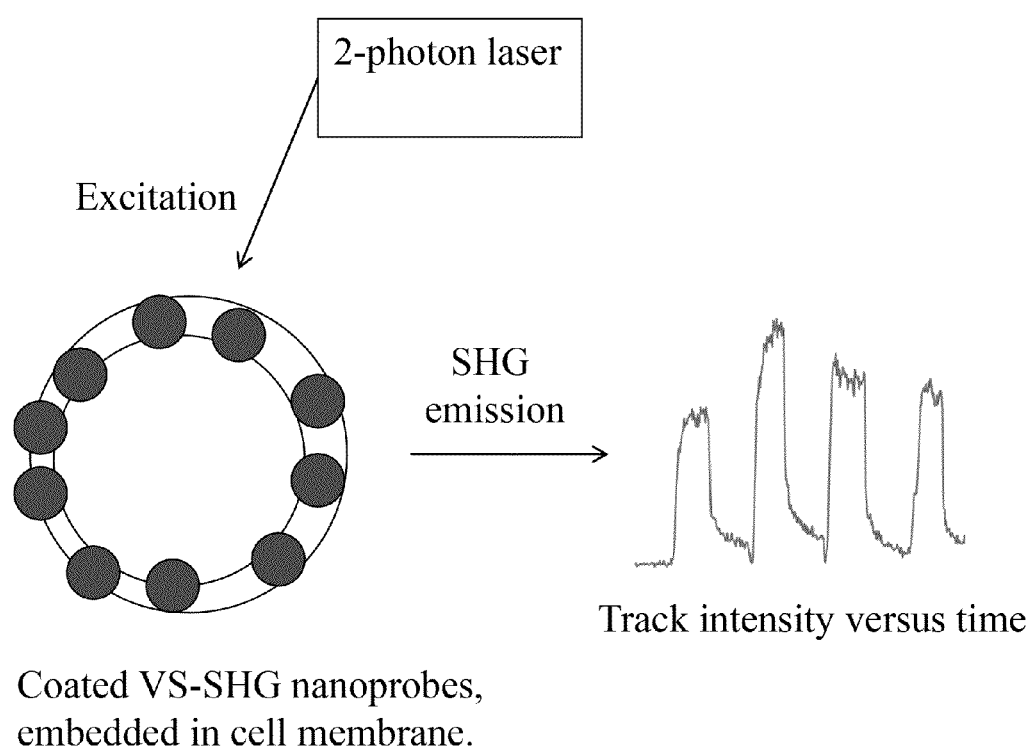
FIG. 10 provides a schematic of the operation of an exemplary embodiment of the VS-SHG nanoprobes in accordance with the current invention.

Third, the VS-SHG nanoparticle would be viewed using the SHG nanoparticle imaging technique described earlier in this application. Any variation in membrane potential would be manifested as a time-dependent change in the transmitted SHG light intensity (as shown in FIG. 10).

Figure 11:
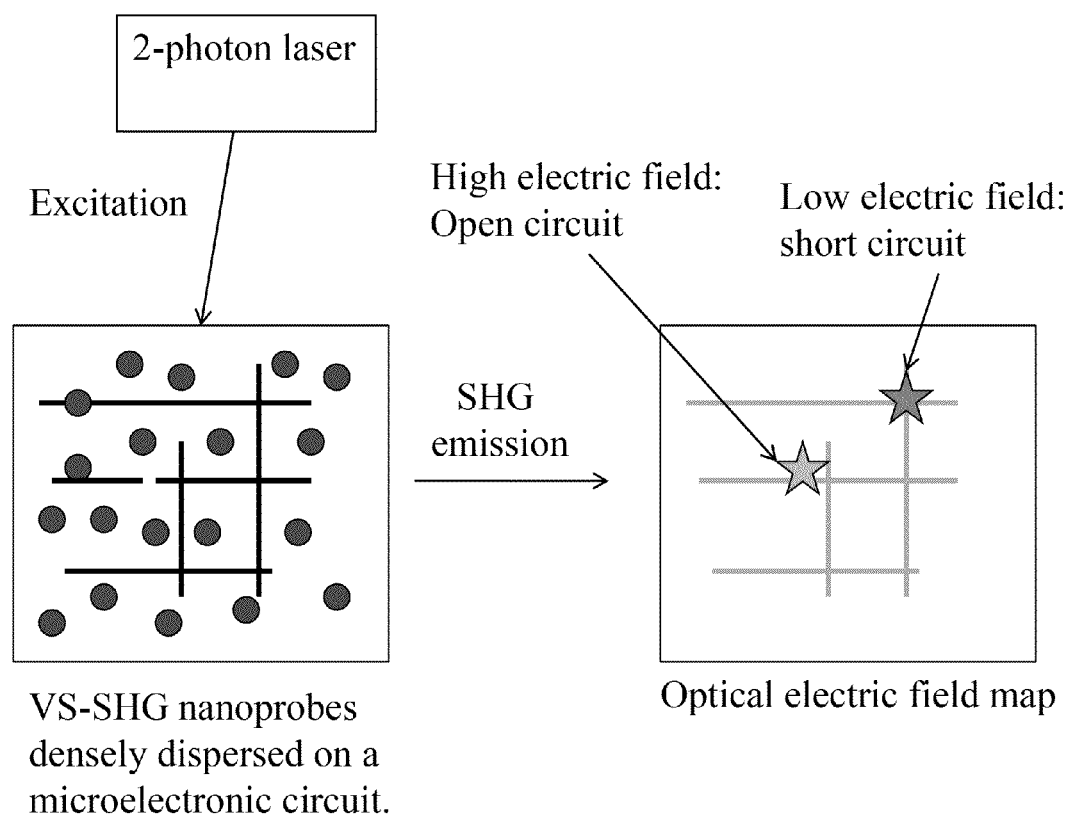
FIG. 11 provides a schematic of an optical. "electric field map" of a circuit as produced using an exemplary VS-SHG system in accordance with the current invention.

In addition, VS-SHG nanoprobes represent a cheap, small, and high-throughput method of rapidly checking microscale and nanoscale electronic circuits for faults. Whenever a new integrated circuit is manufactured it must undergo rigorous testing before being released to the market. If a circuit does not perform to specification, locating troublesome areas can be stymied by the complexity of modern-day circuits; checking each node of the circuit is time-consuming and technically difficult. At the same time, as miniaturization leads to increasingly small devices, distances between components shrink and electric fields increase. Larger electric fields carry the added risk that an electrical short or breakdown effect will occur somewhere in the circuit. This raises the exciting opportunity for optically measuring abnormalities in electric field via VS-SHG nanoparticles, by analyzing an optical "electric field map" of the circuit (as shown in FIG. 11).

An exemplary method for applying VS-SHG nanoprobes in electronic circuit evaluation might involve the following procedures.

First, the VS-SHG nanoparticle material would be selected such that the excitation energy is less than the semiconductor band gap of the electronics. Typically, integrated electronics are made from silicon, which has a band gap of 1.12 electron-volts (eV) at room temperature, so the excitation energy would have to be less than 1.12 eV. This requirement is equivalent to saying that the laser wavelength must be greater than 1106 nm. This restriction is fully compatible with the capabilities of many SHG nanoprobes described in this application. If the integrated electronics are composed of a different material, the two-photon laser excitation wavelength must be adjusted to the appropriate bandgap energy. The above wavelength restriction is necessary to ensure minimal photogeneration of electronic carriers, which could perturb the circuit. If the circuit is insensitive to such perturbations from laser light then the above wavelength restriction is not required.

Second, the VS-SHG nanoparticles would be suspended in a volatile solvent, and uniformly dispersed on the surface of the circuit. The solvent will evaporate leaving behind the bare VS-SHG nanoprobe particles.

Third, an image would be taken of the coated electronic circuit using SHG microscopy. Images will be taken while the circuit is either fully or partially powered on (i.e. in "test" mode). Putative faulty areas of the circuit can then be rapidly identified by image processing took, which will look for abnormalities in the electric field pattern. For example, if two neighboring electronic components are shorted, the electric field pattern will be markedly different than if these components are intact; this will manifest as differences in the optical "electric field map" generated by the VS-SHGs coated on the circuit. Similarly, an open circuit would readily appear as a region of high electric field on the map.

EXAMPLE 6

Functionalization of SHG Nanoprobes

This example demonstrates an exemplary method of how to functionalize and target SHG nanoprobes (here: demonstrated for BaTiO$_3$) including the surface modification of these entities with synthetic polymers (to afford long-circulating properties) and to targeting ligands for selective attachment at desired sites.

The chemicals were obtained from the following sources and used without further purification: tris-2aminoethylphosphonic acid (AEP, Aldrich, 99%), barium titanate (BT, 30-50 nm nanosized powder, Aldrich), methyl-poly (ethylene glycoli-succinimidyl carboxymethyl. (PEG-SCM, 5000 Da, Laysan Bio Inc.) and anhydrous dichloromethane (DCM, Aldrich, 99.8%) solvent.

The surface modification was a two-step process where first the surface of BT nanoparticles was modified with AEP to obtain an amine-coated surface. This was achieved by dispersing barium titanate (0.11 mmol) in ultrapure water (18.3 Mann resistivity, Nanopure Infinity) for 10 min using Branson 220 sonicator. 2-aminoethylphosphonic acid (AEP, 0.13 mmol) was added to the solution and stirred at 80° C. for 1 hr. Particles were separated from the solution by centrifugation (Eppendorf 5810R) at 3500 rpm for 10 min and washed with ultrapure water with sonication at room temperature for 5 min. The washing procedure was repeated trice and the coated nanoparticles (BT-AEP) were dried at 80° C. in air for few hours.

The second modification step included the functionalization of the amine-coated surface of barium titanate nanocrystals (BT-AEP, 14 mg) with PEG-SCM (0.017 mmol) in 10 mL of anhydrous DCM. The solution was stirred at room temperature for 90 min. The solvent was evaporated under vacuum and the solid particles were resuspended in ultrapure water with sonication for 5 min at room temperature. The solution was centrifuged for 10 min at 4000 rpm and room temperature and the washing procedure was repeated twice. Particles were left to dry at 80° C. overnight.

A control experiment was performed to ensure that the zeta potential measurement of the PEGylated barium titanate surface was not due to the electrostatic stabilization of the amine modified barium titanate (BT-AEP) with the PEG-SCM hydrolysis product (PEG-COOH). The PEG-COOH polymer was obtained by hydrolysis of PEG-SCM for 2 hrs in aqueous solution with stirring at room temperature. The excess water was freeze dried under vacuum overnight. To a dispersed aqueous solution of BT-AEP, PEG-COOH (60 mg) was added and stirred for 90 min at room temperature.

Figure 12:
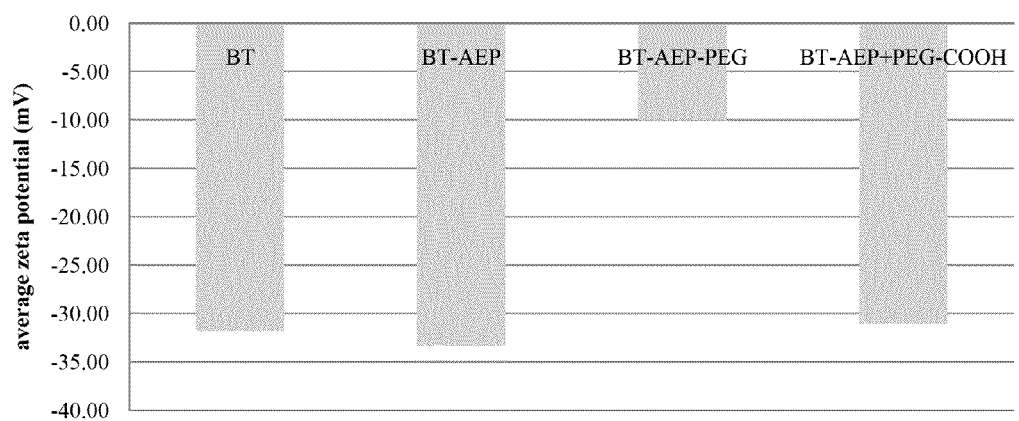
FIG. 12 provides data for the average mean zeta potential reported from two measurement runs with ten cycles each for different modifications of the barium titanate surface.

The nanoparticle aggregate size was measured using dynamic light scattering (ZetaPALS, Brookhaven Instruments Corporation, Holtsville N.Y.) using aqueous dispersions of unmodified and modified barium titanate which were filtered with 450 nm cellulose acetate fillers, apart for the unmodified barium titanate. The stability of the particles in the solution was tested by zeta potential using the ZetaPALS instrument at 27° C. in 1 mM KCl solutions. The results of the zeta potential measurements are presented in FIG. 12 and Table 1 with the control. (BT-AEP+PEG-COOH). The size measurements indicate a decrease in the size of the nanoparticles upon surface modification as presented in Table 2.

TABLE 1

Zeta Potential Measurements BT-AEP

| Sample | Average zeta potential (mV) |
|---|---|
| BT | −31.81 |
| BT-AEP | −33.37 |
| BT-AEP-PEG | −10.04 |
| BT-AEP + PEG-COOH | −31.05 |

TABLE 2

Average Diameter BT

| Sample | Average diameter (nm) |
|---|---|
| BT | 2108.85 |
| BT-AEP | 160.63 |
| BT-AEP-PEG | 119.10 |

Figure 13:
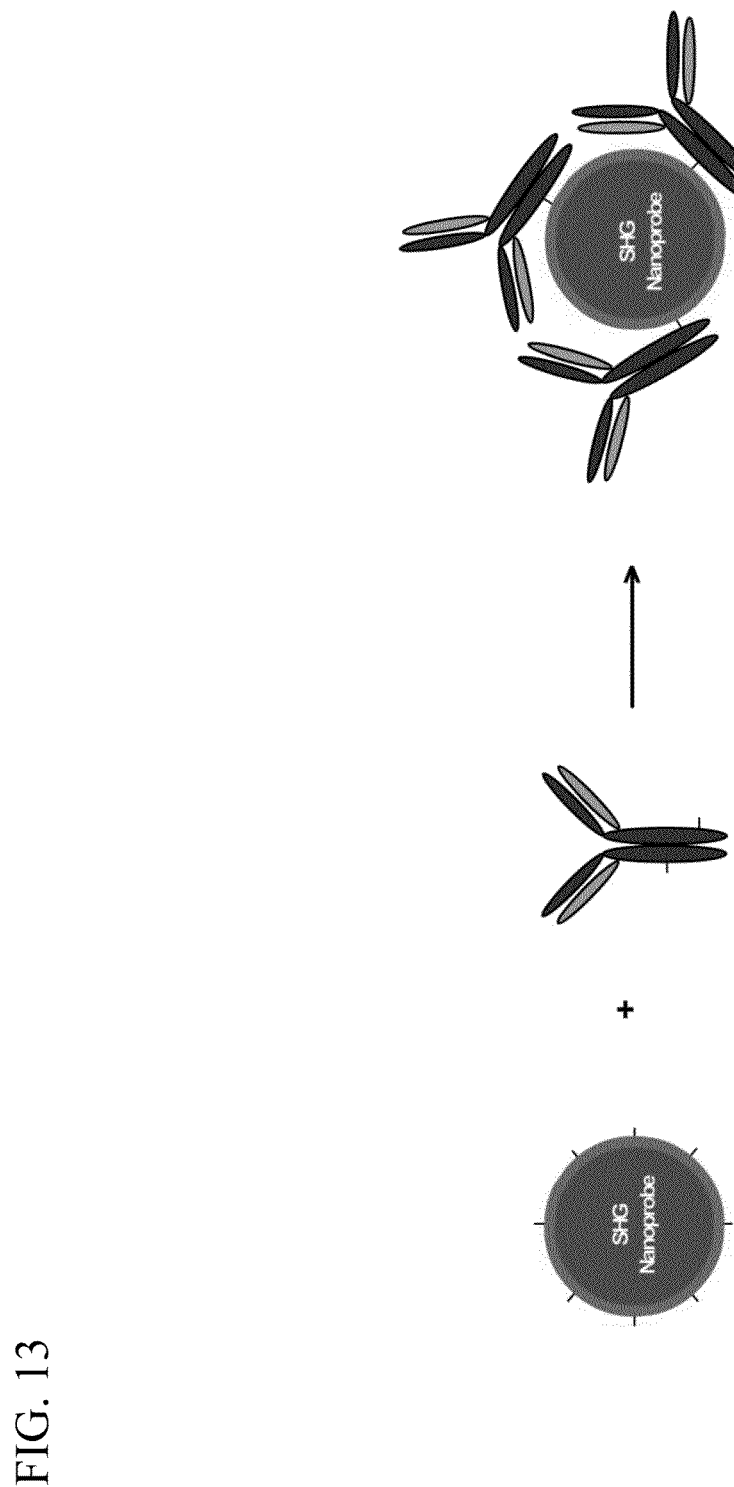
FIG. 13 provides a diagram illustrating the functionalization of SHG nanoprobes to various bio-active species.

Similar approaches can be undertaken for other SHG nanoprobes ultimately resulting in biocompatible, safe, and non-toxic devices for biological applications. The attachment of PEGylated SHG nanoprobes to various bio-active species (protein, DNA, RNA) by (covalent) coupling will require a number of simple PEG analogues at the ends not used for coupling to the particle surface: biotin, bromo, amino, aminoethyl, carboxymethyl, succinimidosuccinate, tosylate, mesylate, aldehyde, actadecylamine, monopalmitate, stearoyloxy derivatives of PEG, as shown in FIG. 13. (See, e.g., J. M. Harris, Zalipsky, S., Poly (*ethylene glycol*): *chemistry and biological applications*. (1997), the disclosure of which is incorporated herein by reference.)

In addition, functionalization may be provided by introducing functional groups on the surface of SHG nanoprobes, including, but are not limited to: sulfhydryl residues, carboxylate groups, primary amine groups, aldehyde residues, and hydrazide functional groups. The targeting may be made by cross-linking reagents, including, but are not limited to: zero-length cross-linkers (among them Carbodiimides), homobifunctional cross-linkers (among them NHS esters, imidoesters), heterobifunctional cross-linkers (among them amine-reactive and sulfhydryl-reactive cross-linkers), and trifunctional cross-linkers (among them sulfo-SBED).

Summary

While the above description contains many specific embodiments of the invention, these should not be construed as limitations on the scope of the invention, but rather as an example of one embodiment thereof. For example, the SHG nanoprobes can be used in conjunction with detection techniques other than the disclosed laser techniques. In addition, the applications of the SHG nanoprobes in accordance with embodiments of the invention are not limited to the FRESH dynamic monitoring technique those described above and can be any kind of biological or other imaging applications in which the SHG nanoprobes may be functionally attached to the target molecule(s). Indeed, it is not necessarily even essential that the nanoprobes of the current invention be attached to the molecules of interest. For example, the nanoprobes could be used to perform cell lineage analysis, which can be performed without attaching the crystals to the proteins. Accordingly, the scope of the invention should be determined not by the embodiments illustrated, but by the appended claims and their equivalent.

DOCTRINE OF EQUIVALENTS

Those skilled in the art will appreciate that the foregoing examples and descriptions of various preferred embodiments of the present invention are merely illustrative of the invention as a whole, and that variations of the present invention may be made within the spirit and scope of the invention. For example, it will be clear to one skilled in the art that alternative SHG imaging techniques or alternative SHG modalities would not affect the improved SHG nanoprobes and imaging techniques of the current invention nor render them unsuitable for their intended purpose. Accordingly, the present invention is not limited to the specific embodiments described herein but, rather, is defined by the scope of the appended claims.

What is claimed is:

1. A second harmonic generating (SHG) nanoprobe system for nucleotide sequencing comprising:
   a plurality of distinct SHG nanoprobes, each of said distinct SHG nanoprobes having no inversion symmetry, the number of such distinct SHG nanoprobes being sufficient such that each distinct nucleotide type to be sequenced has a distinct SHG nanoprobe assigned thereto; and
   an external excitation source for sequentially radiating each of a plurality of nucleotides to be sequenced over at least two distinct excitation wavelengths, wherein the SHG nanoprobes are selected such that the radiation generated by each of the SHG nanoprobes when said nanoprobes are excited at the at least two excitation wavelengths by the external excitation source creates an intensity ratio unique to each said distinct SHG nanoprobe when measured over at least two distinct emission wavelengths;
   a detector configured to detect the sequential emissions of the plurality of distinct SHG nanoprobes at the at least Iwo distinct emission wavelengths; and
   an analyzer for comparing the measured intensities from the sequential emissions at the at least two distinct emission wavelengths to determine a measured intensity ratio, and comparing said measured intensity ratio against a known standard for each of the distinct SHG nanoprobes, thereby sequentially determining each nucleotide in a target sequence.

2. The SHG nanoprobe system of claim 1, wherein each of the SHG nanoprobes is a nanocrystal selected from the group consisting of organic, inorganic and combinations thereof.

3. The SHG nanoprobe system of claim 2, wherein each of the nanocrystals is selected from the group consisting of $BaTiO_3$, SiC, ZnO, ZnS, ZnSe, ZnTe, CdS, CdSe, CdTe, GaAs, GaSb, GaP, GaN, InSb, $LiNbO_3$, $KNbO_3$, $KTiOPO_4$, $Fe(IO_3)_3$, Au, Ag, N-(4-nitrophenyl)-(L)-prolinol (NPP), urea, 4-Nitroaniline, 2-Methyl-4-nitroaniline (MNA), 3-Methyl-4-methoxy-4'-nitrostilbene), $\beta$-$BaB_2O_4$ (Beta-Barium Borate/BBO, $LiB_3O_5$ (Lithium Triborate/LBO), LiNbO3 (Lithium Niobate/LN), KTiOPO4 (Potassium Titanyl Phosphate/KTP), $AgGaS_2$ (Silver Thiogallate/AGS), $AgGaSe_2$ (Silver Gallium Selenide/AGSe), $ZnGeP_2$ (Zinc Germanium Phosphide/ZGP), GaSe (Gallium Selenide), $KH_2PO_4$ (Potassium Dihydrogen Phosphate/KDP), NH4H2PO4 (Ammonium Dihydrogen Phosphate (ADP), KD2PO4 (Deuterated Potassium Dihydroge Phosphate/DKDP), $CsLiB_6O_{10}$ (Cesium Lithium Borate/CLBO), $KTiOAsO_4$ (Potassium Titanyl Arsenate/KTA), $KNbO_3$ (Potassium Niobate/KN), $LiTaO_3$ (Lithium Tantalate/LT), RbTiOAsO4 (Rubidium Titanyl Arsenate/RTA), $BaTiO_3$ (Barium Titanate), $MgBaF_4$ (Magnesium Barium Fluoride), GaAs (Gallium Arsenide), $BiB_3O_6$ (Bismuth Triborate/BIBO), $K_2Al_2B_2O_7$ (Potassium Aluminum Borate/KABO), $KBe_2BO_3F_2$ (Potassium Fluoroborato-beryllate/KBBF), $BaAlBO_3F_2$ (Barium Aluminum Fluoroborate/BABF), $La_2CaB_{10}O_{19}$ (Lanthanum Calcium Borate/LCB), $GdCa_4O(BO_3)_3$ (Gadolinium Calcium Oxyborate/GdCOB), $YCa_4O(BO_3)_3$ (Yttrium Calcium Oxyborate/YCOB), $Li_2B_4O_7$ (Lithium Tetraborate/$LB_4$), $LiRbB_4O_7$ (Lithium Rubidium Tetraborate/$LRB_4$), $CdHg(SCN)_4$ (Cadmium Mercury Thiocyanate/CMTC), $RbTiOPO_4$ (Rubidium Titanyl Phosphate/RTP), $LiInS_2$ (Lithium Thioindate/LIS), $LiInSe_2$ (Lithium Indium Selenide/LISe), $KB_5O_8 \cdot 4H_2O$ (Potassium Pentaborate Tetrahydrate/$KB_5$), $CsB3O5$ (Cesium Triborate/CBO), $C_4H_7D_{12}N_4PO_7$ (Deuterated L-Arginine Phosphate Monohydrate/DLAP), a-$HIO_3$ (a-Iodic Acid), $LiCOOH \cdot H_2O$ (Lithium Formate Monohydrate/LFM), $CsH_2AsO_4$ (Cesium Dihydrogen Arsenate/CDA), $CsD_2AsO_4$ (Deuterated Cesium Dihydrogen Arsenate/DCDA), $RbH_2PO_4$ (Rubidium Dihydrogen Phosphate/RDP), $CsTiOAsO_4$ (Cesium Titanyl Arsenate/CTA), $Ba_2NaNb_5O_{15}$ (Barium Sodium Niobate/BNN), K3Li2Nb5O15 (Potassium Lithium Niobate/KLN), $CO(NH2)_2$ (Urea), $LiIO_3$ (Lithium Iodate), $Ag_3AsS_3$ (Proustite), $HgGa_2S_4$ (Mercury Thiogallate), $CdGeAs_2$ (Cadmium Germanium Arsenide/CGA), $Ti_3AsSe_3$ (Thallium Arsenic Selenide/TAS), CdSe (Cadmium Selenide), ZnO (Zinc Oxide), ZnS (Zinc Sulfide), ZnSe (Zinc Selenide), ZnTe (Zinc Telluride), CdS (Cadmium Sulfide), SiC (Silicon Carbide), GaN (Gallium Nitride), GaSb (Gallium Antimonide).

4. The SHG nanoprobe system of claim 1, wherein each of the SHG nanoprobes include magneto-SHG particles selected from the group consisting of ferromagnetic, ferrimagnetic, paramagnetic, diamagnetic, superparamagnetic (i.e. $Fe_3O_4$), superdiamagnetic, and metamagentic superparamagnetic material.

5. The SHG nanoprobe system of claim 1, wherein each of the SHG nanoprobes are further be surrounded by a resonant material nanoshell, the nanoshell being formed from a material selected from the group consisting of gold, silver, copper, aluminum, palladium, or platinum.

6. The SHG nanoprobe system of claim 1, wherein each of the SHG nanoprobes is less than or equal to 10 μm.

7. The SHG nanoprobe system of claim 1, wherein the excitation source is selected from the group consisting of continuous wave, modulated and pulsed lasers.

8. The SHG nanoprobe system of claim 1, further comprising at least one exciter nanostructure, said exciter nanostructure designed to produce an enhanced local electrical field of a specified frequency when exposed to the excitation source, such that each of the SHG nanoprobes generate a second harmonic resonance emission when brought within range of the resonant electrical field of said exciter nanostructure.

9. The SHG nanoprobe system of claim 8, wherein the at east one exciter nanostructure is a metal nanostructure.

10. The SHG nanoprobe system of claim 9, wherein the metal nanostructure is a nanostructure selected from the group consisting of nanorods, nanospheres or nanoshells.

11. The SHG nanoprobe system of claim 10, wherein the metal nanostructure is made of gold, silver, copper, aluminum, palladium, or platinum.

12. The SHG nanoprobe system of claim 8, wherein each of the SHG nanoprobe and the emitter nanostructure are both attached to a single nucleotide of interest.

13. The SHG nanoprobe system of claim 8, wherein the exciter nanostructure is linked to a polymerase molecule used in the nucleotide sequencing process.

14. The SHG nanoprobe system of claim 8, wherein the exciter nanostructure is disposed on a surface of a detector used for detecting the distinct emissive fingerprints.

15. The SHG nanoprobe system of claim 1, wherein the SHG nanoprobes are functionalized such that the SHG nanoprobe may be attached to the nucleotide of interest.

16. The SHG nanoprobe system of claim 1, wherein the nucleotides are selected from the group consisting of double-stranded DNA, single-stranded DNA, DNA from plasmid, first strand cDNA, total genomic DNA, RNA, cut/end-modified DNA, in vitro transposon tagged DNA.

17. The SHG nanoprobe system of claim 1, wherein the SHG nanoprobes are voltage sensitive SHG nanoprobes, and where the external excitation source is an electric field having sufficient emissive strength to generate a harmonic emission in the SHG nanoprobes.

* * * * *